United States Patent [19]

Hall et al.

[11] Patent Number: 5,800,811
[45] Date of Patent: Sep. 1, 1998

[54] ARTIFICIAL SKIN PREPARED FROM COCLAGEN MATRIX CONTAINING TRANSFORMING GROWTH FACTOR-β HAVING A COLLAGEN BINDING SITE

[76] Inventors: Frederick L. Hall, 345 Pioneer Dr., Suite 1803 W., Glendale, Calif. 91203, Nimni; Marcel E. Nimni, 2800 Neilson Way, #908, Santa Monica, Calif. 90405; Tai-Lan Tuan, 1020 Windsor St., Anaheim, Calif. 92805; Lingtau Wu, 1114 Valencia Way, Arcadia, Calif. 91006; David T. Cheung, 10 W. Palm Dr., Arcadia, Calif. 91007

[21] Appl. No.: 470,837

[22] Filed: Jun. 6, 1995

[51] Int. Cl.$^6$ .............. C12N 5/06; C12N 5/08; C12N 15/00; C12N 11/02
[52] U.S. Cl. .......... 424/93.7; 424/484; 424/85.1; 424/520; 435/69.1; 435/69.7; 435/174; 435/177; 435/366; 435/395
[58] Field of Search .............. 435/174, 177, 435/180, 240.23; 424/423, 424, 425, 426

[56] References Cited

U.S. PATENT DOCUMENTS

| | | | |
|---|---|---|---|
| 4,485,096 | 11/1984 | Bell | 424/95 |
| 4,505,266 | 3/1985 | Yannas et al. | 128/1 R |
| 5,302,701 | 4/1994 | Hidetaka et al. | 530/399 |

FOREIGN PATENT DOCUMENTS

| | | |
|---|---|---|
| 0 293 249 | 11/1988 | European Pat. Off. . |
| 0 433 225 | 6/1991 | European Pat. Off. . |
| WO 94/23740 | 10/1994 | WIPO . |

OTHER PUBLICATIONS

Hochuli E. et al., "Genetic approach to facilitate purification of recombinant proteins with a novel metal chelate adsorbent", Biotechnology, 1988, vol. 6, pp. 1321–1325.

Madisen et al., "Transforming Growth Factor-β2: cDNA Cloning and Sequence Analysis", *DNA*, vol. 7, No. 1, 1988, pp. 1–8.

Derynck, et al., "A new type of transforming growth factor-β, TGF-β3", *The EMBO Journal*, vol. 7, No. 12, pp. 3737–3743, 1988.

Derynck, et al., "Human transforming growth factor-β complementary DNA sequence and epxresssion in normal and transformed cells", *Nature*, vol 316, Aug. 22, 1985,pp. 701–705.

T. Tuan et al., "Expression and Renaturation of Biologically Active Human TGF–Beta Fusion Proteins from *Escherichia Coli*", Research Institute of Children's Hospital Los Angeles, Univ. of S. Cal. Schools of Medicine and Pharmacy, LA.

D. Cheung, et al., "A Biologically Active Collagen–Binding Human TFG–Beta Fusion Protein", Div. of Surgical Research and Orthopedics Children's Hospital of LA/Univ. of S. Cal. Schools of Medicine and Pharmacy, LA.

A. Gray, et al., "Requirement for Activin A and Transforming Growth Factor–β1 Pro–Regions in Homodimer Assembly", *Science*, vol. 247, pp. 1328–1330, 1990.

T. Tuan et al., "Dermal fibroblasts activate keratinocyte outgrowth on collagen gels", *Journal of Cell Science 107*, pp. 2285–2289 (1989).

F. Hall, et al., "High–yield production and renaturation of biologically active human TGF–Beta–1 Fusion Proteins From *Escherichia Coli*", Inventors's Summary prepared for Armour Pharmaceutical Company, Feb. 22, 1994.

L. L. H. Huang–Lee et al., "Crosslinked CNBr–Activated Hyaluronan–Collagen Matrices: Effects on Fibroblast Contraction", *Matrix Biology*, vol. 14/1994, pp. 147–157.

*Primary Examiner*—David M. Naff
*Attorney, Agent, or Firm*—Merchant, Gould, Smith, Edell, Welter & Schmidt

[57] ABSTRACT

An artificial skin is prepared by impregnating a collagen matrix with a transforming growth factor-β having a collagen-binding site to bind the growth factor to the collagen matrix, incubating the impregnated matrix with a source of fibroblasts and mesenchymal stem cells to form a captured population of mesenchymal stem cells within the impregnated matrix and incubating the resultant matrix with a source of keratinocytes which epithelialize the matrix to form an artificial skin. The collagen matrix is preferably in the form of a collagen sheet. The transforming growth factor-β can be transforming growth factor-$β_1$, transforming growth factor-$β_2$ or transforming growth factor-$β_3$. Preferably, the transforming growth factor-β having a collagen binding site is a fusion protein having a purification tag, at least one proteinase site, an extracellular matrix binding site and a transforming growth factor active fragment. The extracellular matrix binding site binds collagen, fibronectin or a cell surface. A method of preparing the fusion protein involves purifying and renaturing transforming growth factor-β protein to provide an active fusion protein.

20 Claims, 1 Drawing Sheet

ARTIFICIAL SKIN PREPARED FROM COCLAGEN MATRIX CONTAINING TRANSFORMING GROWTH FACTOR-β HAVING A COLLAGEN BINDING SITE

BACKGROUND OF THE INVENTION

The Transforming Growth Factor beta (TGFβ) superfamily is a large group of cytokines that exert profound influences on the physiology of wound healing. Their mode of action in wound healing includes the modulation of stem cell populations, as well as their expression of specific genes that encode matrix proteins, cellular receptors, matrix proteinases and proteinase inhibitors. Numerous animal studies have demonstrated the efficacy of exogenous TGFβ in promoting wound healing, which lead to the first clinical applications in the repair of bone, surgical wound healing and in the treatment of diabetic ulcers and burns. Moreover, a single systemic dose of $TGF\beta_1$, given prior to injury (surgery), has been demonstrated to enhance tissue repair and wound healing, suggesting that a single dose, administered systemically before surgery, may improve patient recovery rates.

Clinical studies using $TGF\beta_1$ as a therapeutic agent have been hampered by its limited availability. $TGF\beta_1$ is usually purified from either human platelets, bone or soft tissues such as placenta and kidney. It is estimated that approximately one ton of bone is required to purify enough $TGF\beta_1$ for a single therapeutic treatment. Small amounts of $TGF\beta_1$ have been isolated as a recombinant protein which was processed and secreted by transfected mammalian cells into conditioned growth medium. However, the small amounts of TGFβ obtained and the high cost of production do not make this a method of production commercially viable.

The potential utility of $TGF\beta_1$ as a clinical agent to promote wound healing is complicated by $TGF\beta_1$'s potent chemo-attractant and its macrophage and fibroblast activation properties. At elevated levels of $TGF\beta_1$ such as occur in chronic fibrotic disorders, especially when local inflammation persists, macrophages and fibroblasts accumulate at the site of the disease. Elevated plasma levels of $TGF\beta_1$ has been shown to correlate with a high incidence of hepatic fibrosis, and has also been associated with glomerulosclerosis and pulmonary fibrosis. Therefore, delivery to and activation of $TGF\beta_1$ at the site of a wound is desirable for prolonged treatment with $TGF\beta_1$.

Three distinct TGFβ polypeptides have been identified and are designated $TGF\beta_1$, $TGF\beta_2$ and $TGF\beta_3$. The TGFβ proteins are expressed as precursor molecules of 380, 442 and 410 amino acids, respectively. These inactive latent TGFβ proteins are activated by proteinases such as plasmin, latent $TGF\beta_1$ binding protein (LTBP) and thrombospondin. The mature form of the proteins are dimers of identical polypeptide chains of 112 amino acids in length. The amino acid sequence of the $TGF\beta_1$, $TGF\beta_2$ and $TGF\beta_3$ polypeptides shows 70 to 80% homology and the sequence conserved in the mature polypeptides includes 9 cysteine residues which determine the inter- and intra-polypeptide disulfide bridge formation in the mature proteins.

LTBP and a 60 kD $TGF\beta_1$ binding protein appear to mediate the binding of $TGF\beta_1$ to the extracellular matrix. The close association of $TGF\beta_1$ with the extracellular matrix possibly maintains the elevated growth factor concentration within the local environment of the healing wound.

The use of TGFβ-based medical therapies require the availability of large quantities of pharmaceutical grade TGFβ that is free of transmittable hazards omnipresent in products extracted from animal, in particular human, sources. Therefore, it is desirable to develop a means for preparing large quantities of the mature TGFβ. It is also desirable that the protein is made from a source which eliminates the possibility of hazardous material contaminating the final product. It is also desirable that the protein is engineered to target specific site where wound healing is desired.

SUMMARY OF THE INVENTION

The present invention is directed at a transforming growth factor-β fusion protein, a method of preparation of the transforming growth factor-β fusion protein and methods of using the transforming growth factor-β fusion protein.

The transforming growth factor-β fusion protein comprises a purification tag, at least one proteinase site, an extracellular matrix binding site, and a transforming growth factor active fragment.

The method of preparation transforming growth factor-β fusion protein comprises purifying and renaturing transforming growth factor-β protein to provide an active transforming growth factor-β fusion protein preparation.

Methods of use of the transforming growth factor-β fusion protein include methods to reduce surgery recovery time and the preparation of artificial skin.

BRIEF DESCRIPTION OF THE DRAWINGS

Features, aspects and advantages of the invention will be more fully understood when considered with respect to the following detailed description, appended claims and accompanying drawing where:

DETAILED DESCRIPTION

Figure 1:
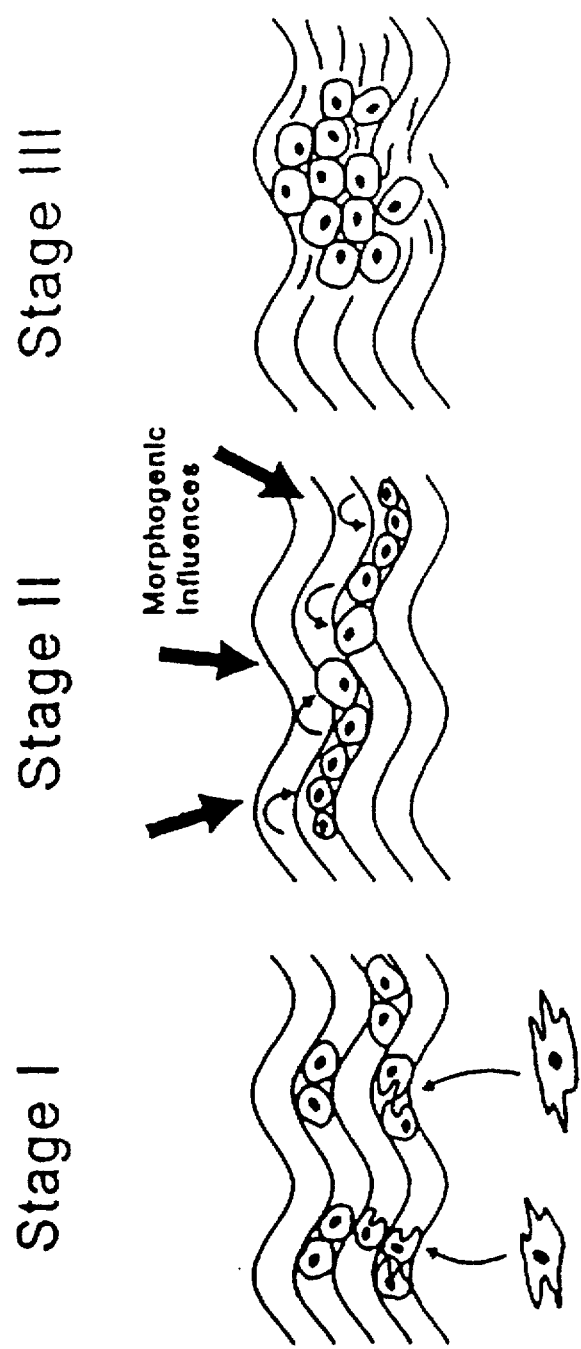
FIG. 1 is a diagrammatic representation of the stages of wound healing observed with TGFβ treated collagen matrices.

This invention is directed at genetically engineering TGFβ fusion proteins, their expression in *E. coli* and their purification and renaturation of active TGFβ. As used herein TGFβ, $TGF\beta_1$, $TGF\beta_2$ and $TGF\beta_3$ or the active fragment of TGFβ, $TGF\beta_1$, $TGF\beta_2$ and $TGF\beta_3$ means the active portion of TGFβ, $TGF\beta_1$, $TGF\beta_2$ and $TGF\beta_3$, respectively, present in the mature form of the naturally occurring proteins or other such proteins which exhibit similar biological activity. Also, as used herein, transforming growth factor-β fusion protein means the active portion of TGFβ, $TGF\beta_1$, $TGF\beta_2$ and $TGF\beta_3$ produced in accordance with this invention and may include other regions such as purification tags, as described below. Transforming growth factor-β fusion protein is also intended to mean the active portion of TGFβ, $TGF\beta_1$, $TGF\beta_2$ and $TGF\beta_3$ which has been cleaved from other domains such as purification tags. The ability to express and renature the active fragment of TGFβ, in the absence of the pro-region, in accordance with the present invention, into a biologically active dimer is a surprising result. Other workers in the field have concluded that their experiments demonstrate that the pro-region of TGFβ is essential for the folding and assembly of TGFβ dimers. Therefore, in view of the teaching in this field expression of the active portion of TGFβ, in the absence of the pro-region, would not be expected to result in a biologically active dimer.

The present invention is also directed at the use of these proteins in the treatment of wound healing.

In accordance with this invention a prokaryotic expression vector is engineered to produce a series of fusion proteins which comprise a cDNA sequence encoding the active fragment of human TGFβ$_1$, TGFβ$_2$, or TGFβ$_3$, by methods well known to those skilled in the art. Additionally, the fusion proteins may comprise a purification tag, proteinase-sensitive linker sites and binding domain such that the protein sequence may contain all or some of the following elements:

purification tag:proteinase site:ECM binding site:proteinase site:TGFβ

Amino acid sequences suitable for use as the elements above are in the sequence listing and are summarized as follows:

Purification tag: SEQ ID NOs: 22, 24, 26 and 28:

Proteinase site: SEQ ID Nos: 1 to 11, 13 and 15;

ECM binding site: SEQ ID Nos: 16, 18 and 20; and

TGFβ: 30, 32 and 34. The inclusion of a purification tag facilitates purification of the fusion protein. A first proteinase site is included to permit cleavage and release of the purification tag after purification of the fusion protein, if desired.

The ECM binding site facilitates delivery of the fusion protein to the desired site of action. The ECM binding site is, therefore, chosen to direct the TGFβ to the site to be healed. Deliver of the TGFβ to the site to be treated reduces the amount of TGFβ required to be administered to be effective and reduces the concentration of circulating TGFβ which may result in undesirable side effects.

In some circumstances it is also desirable to included a second proteinase binding site, which may be the same as or different from the first proteinase site. Where the second proteinase site is different from the first proteinase site, the second proteinase site allows the TGFβ to be released from the ECM binding site once it has reached its site of action. Proteolysis occurs as a result of the action of proteinases released at the site of the injury. Since the release of the proteinases is over a period of time, as the healing process proceeds, the TGFβ is also released slowly, over a period of time. Therefore, a second proteinase inhibitor is used where such "time release" is desirable. In applications where release of the TGFβ is undesirable, the second proteinase site is omitted.

In one embodiment of the present invention extracellular matrix (ECM) binding domains are used which are selective for either collagen (TGFβ-F2), fibronectin (TGFβ-F3) or cell surface. In one embodiment of the present invention the sequence selective for collagen was modified (collagen$^m$), from the naturally occurring sequence of:

Trp-Arg-Glu-Pro-Ser-Phe-Cys-Ala-Leu to:

Trp-Arg-Glu-Pro-Ser-Phe-Met-Ala-Leu to ensure that the Cys would not interfere with the refolding/renaturation of the TGFβ.

Illustrative combinations of fusions proteins suitable for use in the present invention are summarized in Table I. The list in Table I is intended to illustrate the types of fusion proteins which are intended by the present invention and are not intended to limit the scope of the invention. Those skilled in the art will be aware that practice of the present invention could include other elements such as other purification tags, such as epitope tags and specific binding proteins and enzymes ribonuclease S (SEQ ID NO: 24), glutathione S-transferase (SEQ ID NO: 26) and hemagglutinin (SEQ ID NO: 28), other proteinase sites, such as thrombin cleavage site (SEQ ID NO: 14 and 15), factor Xa cleavage site (SEQ ID NO: 12 and 13), plasmin cleavage site (SEQ ID NO: 1), chymotrypsin cleavage site (SEQ ID NO: 2 and 3), elastase cleavage site (SEQ ID NO: 4 and 5), trypsin cleavage site (SEQ ID NO: 6 and 7), pepsin cleavage site (SEQ ID NO: 8 and 9), thermolysin cleavage site (SEQ ID NO: 17), other binding sequences such as cell surface and tissue specific antigens extracellular matrix binding site (SEQ ID NO: 16), fibronectin (SEQ ID NO: 18), collagen (SEQ ID NO: 20); and other TGFβ's fragments, such as TGFβ2 (SEQ ID NO: 32), TGFβ3 (SEQ ID NO: 34), could be substituted for TGFβ$_1$. One skilled in the art will also be aware that modifications of the sequences of these elements could also be used which would not change the functional properties for which they are used. Those skilled in the art will also realize that "linkers" could be added between the elements, to facilitate cloning and manipulation of the resultant clones without changing the functional properties of the resultant fusion proteins.

TABLE I

| Tag | proteinase site | Binding domain | proteinase site | TGFβ | SEQ ID NO. |
|---|---|---|---|---|---|
| (His)$_6$ | none | none | none | TGFβ$_1$ | 22:30 |
| (His)$_6$ | thrombin | none | none | TGFβ$_1$ | 22:15:30 |
| (His)$_6$ | thrombin | collagen$^m$ | none | TGFβ$_1$ | 22:15:20:30 |
| (His)$_6$ | thrombin | collagen$^m$ | thrombin | TGFβ$_1$ | 22:15:20:15:30 |
| (His)$_6$ | thrombin | collagen$^m$ | factor Xa | TGFβ$_1$ | 22:15:20:13:30 |
| (His)$_6$ | factor Xa | none | none | TGFβ$_1$ | 22:13:30 |
| (His)$_6$ | factor Xa | collagen$^m$ | none | TGFβ$_1$ | 22:13:20:30 |
| (His)$_6$ | factor Xa | collagen$^m$ | factor Xa | TGFβ$_1$ | 22:13:20:13:30 |
| (His)$_6$ | factor Xa | collagen$^m$ | thrombin | TGFβ$_1$ | 22:13:20:15:30 |
| (His)$_6$ | thrombin | fibronectin | none | TGFβ$_1$ | 22:15:18:30 |
| (His)$_6$ | thrombin | fibronectin | thrombin | TGFβ$_1$ | 22:15:18:15:30 |
| (His)$_6$ | thrombin | fibronectin | factor Xa | TGFβ$_1$ | 22:15:18:13:30 |
| (His)$_6$ | factor Xa | fibronectin | none | TGFβ$_1$ | 22:13:18:30 |
| (His)$_6$ | factor Xa | fibronectin | factor Xa | TGFβ$_1$ | 22:13:18:13:30 |
| (His)$_6$ | factor Xa | fibronectin | thrombin | TGFβ$_1$ | 22:13:18:15:30 |

In the practice of the present invention, fusion protein expression vectors are expressed in E. coli or other suitable hosts and are isolated and purified. The proteins of the present invention expressed in bacteria accumulate in inclusion bodies in a precipitated form. In such cases it is desirable to solubilize the protein in a denaturing, or other suitable buffer for further purification. Such denaturing buffers include a denaturing agent such as 8M urea and may also include reducing agents such a, dithiothreitol (DTT) or β-mercaptoethanol.

In one embodiment of the present invention the purification of the fusion proteins uses a purification tag comprising polyhistidine expressed as an N-terminal portion of the fusion protein. When the purification tag comprises polyhistidine, a metal chelate binding medium such as nickel chelate medium is used as the purification medium. In other embodiments of the present invention the purification tag comprises epitopes, schistosoma japonicum glutathione S transferase (GST)ribonuclease S or Hemagglutinin, and the binding medium comprises PBS with an eluting agent such as low pH, peptides or glutathione. Other purification tags, their associated binding media and suitable conditions for binding and eluting the proteins from the media are summarized in Table II.

TABLE II

| Tag | Binding Medium | Binding Buffer | Elution Buffer |
|---|---|---|---|
| (His)$_6$ | metal chelate | denaturing buffer, pH 6.5 | denaturing buffer, pH 4.0 |
| Ribonuclease S | S-protein agarose | PBS | PBS + low pH or peptides |
| GST | affinity medium | PBS | PBS + low pH or glutathione |
| Hemagglutinin A | Immuno-affinity | PBS | PBS + low pH or peptides |

Proteins are isolated from host cells transformed with TGFβ fusion protein expression vector and proteins are solubilized in a denaturation buffer adjusted to a pH of about pH 8.0. Suitable denaturation buffers are comprise a high concentration of a denaturant such as 8M urea. Such buffers may also comprise a reducing agent such as β-mercaptoethanol. Any particulate material in the solubilized protein sample is removed by centrifugation at about 20,000×g for about 20 minutes.

The supernatant, which includes TGF-fusion protein, is collected and mixed with a metal chelate medium such as Ni-NTA resin and gently agitated for about 1 hour. The TGF-fusion protein/resin mixture is then loaded onto a column, the resin is allowed to settle and the liquid is drained off. The protein/resin mixture is washed with denaturation buffer adjusted to a pH of about 8.0 to remove non-specifically bound proteins. Additional non-specifically bound proteins are eluted by washing the protein/resin mixture with denaturation buffer, adjusted to pH of about 6.5. The TGF-fusion protein is then eluted from the metal chelate medium by washing with denaturation buffer adjusted to a pH of about 4.0 and the eluted proteins, which include TGFβ, are collected.

The eluate is diluted to a protein concentration of about 0.05 to about 0.5 mg/ml with denaturation buffer and adjusted to a pH of about 8.0. The diluted protein sample is then further diluted with about 4 volumes of freshly made buffer such as about 20 mM Tris-HCl, pH 8.0, about 250 mM NaCl, about 0.05% (v/v) NP-40, about 2 mM reduced glutathione and about 0.2 mM oxidized glutathione.

The diluted protein is sealed in a container and stored overnight at about 4° C. The diluted protein is then dialyzed against an equal volume of a dialysis buffer such as about 20 mM Tris, pH 8.0, about 250 mM NaCl and about 20% (v/v) glycerol for about 20 minutes. After about 20 minutes, and then about every 20 minutes thereafter, the dialysis buffer is replaced with twice the volume of dialysis buffer previously used, until the final volume is about 10 times the volume of the dialysate. The dialysis is then stored overnight at about 4° C. without stirring. The next morning the dialysis is stirred for about 30 minutes. The dialysis buffer is then replaced and the dialysis is stirred for about 2 hours. The contents of the dialysis bag is then collected and any particulate matter is removed by centrifugation at about 5,000 rpm for about 20 minutes at 4° C.

The TGFβ fusion protein isolated, purified and renatured as described above, exhibits an antiproliferative activity comparable to TGFβ$_1$ controls (naturally occurring TGFβ$_1$).

The present invention is also directed at the use of TGFβ fusion proteins in wound healing.

It is desirable to administer the TGFβ of the present invention as a preventative measure prior to surgery. In such cases, TGFβ prepared in accordance with the process of the present invention, is administered as a single dose of 100 to 500 μg/ml/kg body weight, intravenously, about 24 hours prior to surgery.

The present invention is also directed at a mesenchymal stem cell trap. FIG. 1 is a diagram of wound healing stages observed within TGFβ treated collagen matrices. Depicted are three major features: (I) recruitment and expansion of a mesenchymal stem cell (MSC) population, (II) elaboration (of factors) and differentiation of cellular phenotype and (III) resolution and remodeling of the extracellular matrix. TGFβ impregnated collagen matrices are utilized to selectively reinforce the proliferation of mesenchymal stem cells that are present in low abundance within human bone marrow aspirates under conditions where the remainder of the cellular components of the marrow do not survive. Rescue and selection of TGFβ responsive stem cells from human bone marrow aspirates is performed after about 15 days of serum deprivation. Serum deprivation results in the death of unwanted cells.

The present invention is also directed at the use of genetically engineered TGFβ fusion proteins, produced in prokaryotes, for therapeutic advantage in the clinical management of ex vivo histogenesis, the preparation of "Artificial Skin" and surgical wound healing. Collagen matrices and sheets which are currently used as a "skin or tissue replacement", though optimal in terms of structural integrity and biodegradability, are highly antigenic in wound healing applications, resulting in inflammatory responses (rejection) and fibrosis (scarring). In contrast, TGFβ impregnated collagen matrices inhibit inflammatory processes while promoting angiogenesis and histogenesis. TGFβ is a natural and critical component regulating epithelial-mesenchymal interactions in the developmental morphogenesis of skin appendages. Collagen bound TGFβ-F2 fusion proteins function effectively to select and expand (capture) a population of mesenchymal stem cells in vitro.

An autologous "artificial" skin is prepared by selecting and expanding a population of explanted human fibroblasts, along with other resident mesenchymal precursors, within TGFβ impregnated collagen sheets. This procedure is continued in vitro up to an optimized point whereby the collagen sheet is effectively cellularized yet not degraded. At or just prior to this point, the collagen/connective tissue sheet is epithelialized by the application of an explanted plug of keratinocytes.

The human artificial skin comprised of TGFβ impregnated matrix such as collagen sheets is cellularized and epithelialized in a 2-stage process:

1. Enrichment (recruitment and expansion) of pluripotent stem cells facilitate normal histogenesis and wound healing. Recombinant TGFβ fusion proteins are applied to the cellularized "skin" (i.e., cellularized/epithelialized collagen sheets) and/or the wound surface.
2. Secondary application of TGFβ fusion proteins inhibits rejection and promotes fusion of cultured tissues. The timing of each stage of the ex vivo tissue culture, as well as the thickness and physiochemistry of the collagen sheets, are determined by visual observation. The TGFβ fusion proteins play a pivotal role in promoting normal skin healing while suppressing the inflammatory responses and granulation tissue associated with chronic wounds.

EXAMPLE 1

Recombinant Constructs and Protein Expression

Cytoplasmic RNAs isolated from EW-1 Ewing's sarcoma cells and human MG-63 osteosarcoma cells were reverse transcribed into first-strand cDNA using an antisense oligonucleotide primer, by methods well know to those skilled in the art. PCR amplification was performed on the first strand cDNA and the resulting PCR products were separated electrophoretically, by methods well know to those skilled in the art. Visualized bands were purified from agarose gel by Geneclean (Bio 101) and ligated to a TA vector (Invitrogen). Color-selected clones were isolated and analyzed by restriction mapping, followed by nucleotide sequence determination.

To construct a tripartite fusion protein the cDNA sequence encoding the C-terminal 112 amino acids of human $TGF\beta_1$, obtained by RT-PCR, was ligated in frame to pET28 vector (Novagen), and maintained in the XL Blue strain of *E. coli* BL21(DE3). The orientation and reading frame of the insert was confirmed by DNA sequence analysis.

Each of the pET-$TGF\beta_1$ constructs were transformed into *E. coli* BL21(DE3), and high level expression of recombinant proteins was induced in the presence of 0.4 mM isopropyl thiogalactopyranoside (IPTG) for 5 hours at 37° C. with shaking at 300 rpm. The first construct, pET-$TGF\beta_1$-F1, contained a $(His)_6$ leader sequence at the N-terminus of the fusion protein, a thrombin cleavage site in the first proteinase site, followed by a truncated active $TGF\beta_1$, fragment (i.e. the plasmid encoded SEQ ID NOs. 22:15:30). Two additional constructs, pET-$TGF\beta_1$-F2 and pET-$TGF\beta_1$-F3, incorporating collagen-binding and fibronectin-binding sites, respectively (i.e. the plasmids encoded SEQ ID NOs. 22:15:20:30 and SEQ ID NOs. 22:15:18:30, respectively), were designed for extracellular matrix targeting of these fusion proteins.

EXAMPLE 2

Small Scale Induction of Recombinant TGFβ Fusion Proteins in *E. coli*

*E. coli*, BL21(DE3), transformed with pET-$TGF\beta_1$-F1, prepared as described above, with a protein tag of 6 Histidine residues at the N-terminal of the fusion protein was inoculated into 5 ml of 2×YT medium in the presence of kanamycin (50 µg/ml kanamycin sulfate, supplied by GIBCO-BRL). The cultures were incubated at 37° C. with shaking (225 rpm; Lab-Line orbital shaker) until visible bacterial growth was observed, about 2 to 3 hours.

Three ml of cell suspension was transferred to 12 ml of YT medium which included 50 µg/ml kanamycin sulfate. The cultures were incubated at 37° C. with shaking (225 rpm) until visible bacterial growth was observed, about 2 to 3 hours. The cultures were then cultures were then monitored at $A_{600}$. When the cultures reached $A_{600}$ of 0.6 to 0.8 the expression of the fusion protein was induced by the addition of IPTG (Sigma I-6758) to a final concentration of 0.4 mM. The cultures were incubated at 37° C. with shaking at 300 rpm.

The remaining 2 ml of the original culture, the pre-induction samples, were centrifuged in a microfuge (Eppendorf 5415C) at 10,000 rpm for 2 minute and the supernatant aspirated. Two hundred µl of SDS sample buffer (reducing) was added to the cell pellet and the sample was mixed and heated at 95° C. to 98° C. for 7 minutes. The pre-induced samples were stored at −20° C. until needed.

After 3.5 to 4 hours of incubation in the presence of IPTG, 1 ml aliquots of the cultures were removed and centrifuged as described above for the uninduced samples. The cell pellet was dissolved in 300 µl SDS sample buffer (reducing) and heat at 95° C. to 98° C. for 7 minute. The induced samples were stored at −20° C. until needed.

The remainder of the cells were collected by centrifugation at 2,000 to 3,000 rpm for 10 minute. The cell pellets were frozen at −200° C. until needed.

EXAMPLE 3

Gel Electrophoresis and Protein Staining

Ten µl of each of the pre-induction and induced samples prepared as described in Example 2, were loaded, per lane, on a 8 to 16% gradient gel (1.5 mm thick). Five to 10 µl of protein standard (e.g., Novex) were included on the gel in separate lanes. The gels were run in standard SDS gel electrophoresis buffer at 100 to 125 volts for 2 to 2.5 hours until the dye front reached the bottom of the gel. The gel was fixed in 40% (v/v) methanol, 10% (v/v) acetic acid for 20 minutes with gentle shaking. The gel was then stained with 0.25% (w/v) Coomassie blue stain (in 50% (v/v) methanol, 10% (v/v) acetic acid) for 20 minutes. The gel was then destain twice (1 to 2 hours each time) in 40% (v/v) methanol, 10% (v/v) acetic acid. The gels were then viewed over a light box to determine, qualitatively, the level of induction.

Finally, the gel was destained overnight in 10% (v/v) methanol, 10% (v/v) acetic acid, dried and stored.

EXAMPLE 4

Small Scale Induction of Recombinant TGFβ Fusion Proteins in *E. coli*

A clone with a high induction response determined by the process of Examples 1 to 3 was selected and 200 µl of a 3 to 4 hour culture was added to 20 ml of medium supplemented with 50 µg/ml kanamycin. The culture was incubated at 37° C. with shaking at 225 rpm overnight. Ten ml of the overnight culture was inoculated into 500 ml medium supplemented with 50 µg/ml kanamycin. The $A_{600}$ of the cells was monitored. When the $A_{600}$ reached 0.7 to 0.8, 1 ml aliquots were collected, centrifuged and the cell pellet denatured as described in Example 2. This sample represented the pre-induction sample.

Five hundred µl IPTG was added to the culture and the culture was incubated with shaking at 275 rpm for 4 to 5 hours. A 1 ml aliquot was collected for the induced sample.

Cells in the remaining culture were collected by centrifugation at 4° C. at 8,000 rpm (7,500×g) for 15 minute. The supernatant was decanted and the cell pellets were stored at −20° C.

Induction of the pET-$TGF\beta_1$-F1 fusion protein in the BL21(DE3) strain of *E. coli* in the presence of IPTG resulted in high yield expression of the 12.5 kD His-tagged C-terminal active fragment of $TGF\beta_1$. The vast majority of the expressed protein was found sequestered in insoluble inclusion bodies in the *E. coli*. The expressed protein was recovered by solubilization in 8 M urea followed by Ni-NTA chelate chromatography.

EXAMPLE 5

Renaturation of Recombinant $TGF\beta_1$-F1

Solubilization and refolding of recombinant $TGF\beta_1$-F1 fusion protein was performed under a variety of experimental conditions.

Method I: A single step method used low concentrations of urea and DTT.

Method II: A redox system used DTT in conjunction with glutathione.

Method III: A modification of the glutathione redox system involved a slow dilution of the urea-solubilized material (solubilized in 10 mM Tris base, 100 mM $Na_2HPO_4$, and 8M urea, pH 8.0) with a balanced redox buffer (2 mM reduced glutathione, 0.2 mM oxidized glutathione, 20 mM Tris-HCl, pH 8, 250 mM NaCl, 0.05%NP-40; NP-40 supplied by Sigma N0896 for 48 hours prior to dialysis).

In each case, the renatured preparation was dialyzed in protracted steps against Tris buffer (20 mM Tris-HCl, pH 8.0, 500 mM NaCl, 0.05% NP-40, and 10% glycerol), and further purified by nickel chelate chromatography on a Ni-NTA (Qiagen) medium. Non-specifically bound proteins were removed from the protein bound medium by washing with 20 mM Tris-HCl buffer, pH 8, containing 25 mM imidazole, 500 mM NaCl, and 10% glycerol. After non-specifically bound proteins were removed from the medium the bound fusion protein was eluted with 20 mM Tris-HCl buffer, pH 8, containing 500 mM imidazole, 500 mM NaCl, and 10% glycerol.

Attempts were made to refold $TGF\beta_1$-F1 using various refolding schemes which had previously been successful with renaturing other proteins.

Solubilizing the inclusion bodies in 2M urea and 2 mM DTT (Method I) was effective in renaturing other proteins (IGF-1: Chang et al. In: *Protein Folding In Vivo and in Vitro*, ed by Cleland, J. L., Symposium Series 526, American Chemical Society, Washington D.C., pp. 178–188, 1993, which is incorporated herein by reference) but did not produce an appreciable amount of biologically active $TGF\beta_1$.

Refolding/reoxidation of $TGF\beta_1$-F1 in the presence of glutathione and DTT as described by Glocker et al. (*J. Biol. Chem.* 91, 5868–5872, 1994; Method II, which is incorporated herein by reference) yielded a very small amount of renatured $TGF\beta_1$ with little biological activity.

Method III, refolding the urea-solubilized aggregates from inclusion bodies at a protein concentration of 0.1 mg/ml in an optimized glutathione redox couple system (2 mM reduced: 0.2 mM oxidized) was determined to be the most effective method for renaturation of the isolated $TGF\beta$.

Renaturation of the $TGF\beta_1$ fusion protein (~13 kD) into soluble homodimers (~30 kD) was demonstrated by SDS-PAGE performed under non-reducing conditions.

Biological activity of the renatured recombinant $TGF\beta_1$ fusion protein was confirmed by an Mv1Lu cell proliferation assay (Example 7) in which purified human platelet $TGF\beta_1$ served as a positive control. Dialyzed protein fractions (5 to 30 µg/ml) from the glutathione redox-couple refolding system (Method III) exhibited an anti-proliferative activity comparable to the $TGF\beta_1$ control treatments (50 to 200 pg/ml) in Mv1Lu cells. In contrast, fractions from Methods I and II, respectively, exhibited little or no biological activity. The inability of these fractions to inhibit Mv1Lu cell proliferation indicated that there was no effect of the final dialysis buffer components, at these dilutions, on Mv1Lu cell proliferation activity.

The biological activity of renatured $TGF\beta_1$ in solution, and when it was adsorbed onto collagen- or fibronectin-coated surfaces were examined. In solution, renatured recombinant $TGF\beta_1$ (by Method III) exhibited an anti-proliferative effect on Mv1Lu cells. Mv1Lu cells are highly efficient at adhesion and proliferation on collagen- or fibronectin-coated surfaces. $TGF\beta_1$ adsorbed onto collagen and/or fibronectin exerts a similarly potent antiproliferative effect on Mv1Lu cells (~70% on collagen and ~40% on fibronectin) without affecting the ability of these cells to adhere to these surfaces.

EXAMPLE 6

Extraction, Purification and Renaturation of Biologically Active $TGF\beta$ Fusion Proteins in High Yield from *E. coli* Inclusion Bodies Frozen *E. coli* pellets, transformed with $TGF\beta_1$-F1 or $TGF\beta_1$-F2 of induced cultures, prepared as described in Example 4, were suspended in 25 ml of lysis buffer (20 mM Tris, pH 8.0, 250 mM NaCl, 0.05% (v/v) NP-40, 0.4 mM PMSF, 25 µl β-mercaptoethanol, 10 mg lysozyme) at 4° C., and incubated at 4° C. for 30 minutes with constant stirring. The suspension was transferred to 50 ml centrifuge tubes and sonicated with a Polytron-sonicate, at a setting of #7 or 25,000 rpm (two cycles of 30 seconds) at 4° C. The sonicated lysate was then centrifuged at 12,000×g at 4° C. for 20 minutes. The supernatant was decanted and the pellet, which included inclusion bodies, were washed with Basic Binding buffer (20 mM Tris-HCl, pH 8.0, 250 mM NaCl, 0.05% (v/v) NP-40) at 4° C. and centrifuged at 12,000×g for 20 minutes.

The pellet, which included inclusion bodies, was suspended in 25 ml of denaturation buffer (8M urea, 0.1M sodium phosphate, 10 mM Tris, pH 8.0, made fresh daily by passing a stock 8M urea solution (480 g/l of warm $dH_2O$) through a Mix-bed resin (TMD-8, Sigma) just before use and prior to the addition of the buffers. Seventeen µl of β-mercaptoethanol was added and the solution was vortexed vigorously until most of the pellet was dissolved.

The solution was then centrifuged at 20,000×g for 20 minutes at room temperature and the supernatant was collected.

About 5 µl of the supernatant was aliquoted into a microfuge tube, and 795 µl of water and 200 µl of BioRad Protein Assay Reagent was added, mixed well and the samples were read at 595 nm in a spectrophotometer using 5 µl of denaturation buffer, 790 µl of water and 200 µl of BioRad Protein Assay Reagent as a blank. The protein concentration was estimated from a protein standard curve.

The supernatant, which included the TGF fusion protein, was mixed with Ni-NTA resin (5 ml bed volume, equilibrated with denaturation buffer) in a 50 ml centrifuge tube and rocked for 1 hour at room temperature. The TGF fusion protein/resin mixture was loaded onto a 25 ml column, and the resin was allowed to settle and the liquid to drain off. The TGF-fusion protein/resin was washed with 40 ml of denaturation buffer, pH 8.0.

The TGF-fusion protein/resin was then washed with 30 ml of Ni-chelating column wash buffer A (denaturation buffer, adjusted to pH 6.5 with 2M HCl, made fresh daily). The TGF-fusion protein was eluted from the resin with Ni-chelating column Elution buffer B (denaturation buffer adjusted to pH 4.0 with 2M HCl, made fresh daily). One ml fractions were collected. The protein concentration of 5 µl of each fraction was determined as described above.

Fractions with protein readings greater than 0.1 mg/ml were pooled. The volume was measured and the protein concentration of the pooled fractions was determined as described above.

The pooled fractions were diluted with denaturation buffer, pH 8.0 to a final protein concentration of <0.5 mg/ml (<0.1 mg/ml for F2 constructs). The pooled samples were then further diluted with 4 volumes of freshly made Redox Buffer (20 mM Tris-HCl, pH 8.0, 250 mM NaCl, 0.05%

(v/v) NP-40, 2 mM reduced glutathione, 0.2 mM oxidized glutathione) dropwise on ice with vigorous mixing.

The diluted protein was sealed in a container and stored overnight at 4° C. The diluted protein was then dialyzed against an equal volume of dialysis buffer (20 mM Tris, pH 8.0, 250 mM NaCl, 20% (v/v) glycerol) for 20 minutes. After 20 minutes, and every 20 minutes thereafter, the dialysis buffer was replaced with twice the volume of dialysis buffer previously used, until the volume of the dialysis buffer was 1 liter. The dialysis was then stored overnight at about 4° C. without stirring. The next morning the dialysis was stirred for 30 minutes. The dialysis buffer was replaced and the dialysis was stirred for 2 hours. The contents of the dialysis bag was collected, centrifuged at 5,000 rpm for 20 minutes at 4° C. and the supernatant was collected. The protein concentration of the collected supernatant was determined and the supernatant was stored at −70° C.

Induction of the $TGF\beta_1$-F2 fusion protein in the BL21 (DE3) strain of $E.\ coli$ yielded high levels of expression of the 12.5 kD polypeptide which was found in inclusion bodies. The inclusion bodies were solubilized in 8M urea and purified by Ni-NTA metal chelate chromatography. Similar to the $TGF\beta_1$-F1 fusion protein, pure $TGF\beta_1$-F2 protein was extracted, as demonstrated by a single 12.5 kD band on SDS-PAGE, in the presence of DTT. Upon oxidative refolding and dialysis, approximately 15 mg of pure soluble protein was obtained from a 250 ml bacterial culture.

To evaluate the kinetics of refolding, samples were taken at specific time intervals after the initiation of refolding and iodoacetamide (50 mM) was added immediately to block further reaction of the sulfhydryl groups. The samples were stored at 4° C. until analyzed by non-reducing SDS-PAGE. Dimers began to form after 2 hours of refolding, reaching maximal levels at 4 to 10 hours under the conditions described above.

Renaturation and assembly of the $TGF\beta_1$-F2 polypeptide (12.5 kD) into active soluble homodimers (25 kD) was demonstrated in the Mv1Lu cell proliferation assay in which commercially available purified human platelet $TGF\beta_1$ served as a positive control. The $TGF\beta_1$-F2 fusion protein renatured from bacterial inclusion bodies by the glutathione redox refolding method exhibited an anti-proliferative activity comparable to the $TGF\beta_1$ control treatments, although the specific activity of the recombinant growth factor preparation was considerably (~300 times) lower. Renatured $TGF\beta_1$-F2 fusion protein bound to collagen-coated wells also inhibited the proliferation of Mv1Lu cells. However, the level of inhibition observed for collagen-bound growth factor was much smaller than that observed when the unbound $TGF\beta_1$-F2 protein was added directly to the culture medium.

EXAMPLE 7

Bioassay for TGFβ Antiproliferative Effect on Mink Lung Epithelial-Like Cells (mv1lu)

Mink lung epithelial-like cells (Mv1Lu; American Type Culture Collection No. ATCC CCL64) were grown to a subconfluent density (80%) in DMEM (GIBCO) with 10% (v/v) fetal calf serum (FCS). The medium also contained Gentamicin (50 μg/ml) and Fungizone (20 μg/ml). The cells were harvested by trypsinizing, in 0.25% (w/v) trypsin, 1 mM EDTA in Hanks BSS (Gibco/BRL) and plated in a 24 well flat-bottomed cell culture plates, with 100 to 150×10³ cells/well, in DMEM with 10% (v/v) FCS.

Positive control assays included human recombinant TGFβ in assay medium (0.1% (v/v) FCS in DMEM with 2 to 250 pg TGFβ/ml). Negative controls included no human recombinant TGFβ (0 TGFβ/ml) and dialysis buffer was added instead of TGFβ.

Samples were serially diluted into the assay medium. Cells were rinsed twice with DMEM and assay media was added (500 μl/well for controls and testing samples). The plates were incubated at 37° C. with 5% (v/v) $CO_2$ for 20 hours.

³H-Thymidine (ICN, Cat. # 2407005, 1 mCi/ml) uptake assays were performed by adding 20 μl/well (1 μCi) of ³H-thymidine and the incubation was continued for an additional 4 hours.

The media was removed and discarded. The wells were washed, three times, each for 10 minutes with 1.5 ml of cold 10% (w/v) trichloroacetic acid (TCA) and washed once with water. Five hundred μl of 0.2M NaOH was added to each well and the samples were incubated at 37° C. for 1 hour. The samples were checked visually to determine if the cells were solubilized. If they were not, they were further incubated at 37° C. until solubilized.

At the end of the solubilization the samples were mixed gently and 200 μl of the contents of each well was added to a scintillation vial. An equal volume of 0.5M acetic acid was then added to each sample and the samples were mixed. Scintillant (Ready Safe) was added to each of the samples and they were count for two minutes in a scintillation counter. After storage in the dark overnight the samples were again counted for 2 minutes.

EXAMPLE 8

Epithelialization of Collagen Gels with Human Keratinocyte Buttons

TGFβ treated collagen carrier stem cell trap was prepared as follows: $TGF\beta_1$ (20 ng/ml) and $TGF\beta_1$-F2 fusion protein (25 μg/ml) were reconstituted in DMEM and 200 μl of $TGF\beta_1$ or $TGF\beta_1$-F2 was added to collagen carrier immobilized in 24 well cell culture plates. The samples were incubated for 2 hours at 22° C. At the end of the incubation, the wells, which included the samples, were rinsed twice with 1 ml each of DMEM. The DMEM medium also included Gentamicin (50 μg/ml) and Fungizone (20 μg/ml).

Dermal fibroblasts/mesenchymal cells were harvested as follows: Fresh human skin from surgery was collected and rinsed twice with sterile phosphate buffered saline (PBS). The adipose tissue was excised and the skin was cut into 4 mm×10 mm samples. The skin samples were incubated in prewarmed 0.5w (w/v) dispase/DMEM (10 ml for 2×2 cm² skin) at 37° C. for 90 minutes with agitation. At the end of the incubation, the keratinocyte layer was peeled off using fine forceps and stored on ice cold DMEM until required.

The dermis was incubated in collagenase-dispase solution (0.5% (w/v) dispase and 1,000 units/ml collagenase) in PBS for an additional 2 hours with agitation (10 ml for 2×2 cm² skin). At the end of the incubation, the collagenase/dispase was neutralized by the addition of FCS to a final concentration of 10% (v/v). The samples were then gently homogenized by drawing the mixture into a pipette and releasing it 20 times. The mixture was then filtered through a 100μ mesh filter and centrifuged to collect cells.

The cells were resuspended in 0.5% (v/v) FCS/DMEM and plated at 200×10³ cells/ml/well/collagen carrier. The plates were then incubated at 37° C. with 5% (v/v) $CO_2$ overnight.

At the end of the overnight incubation the medium was replaced with fresh 0.5% (v/v) FCS/DMEM. The plates were then incubated for an additional 1 to 3 days.

Keratinocyte buttons were prepared as follows: Fresh keratinocyte sheet from human skin was harvested, as described above. The keratinocyte sheet was cut into 2×2 mm² buttons. Medium was removed from each of the above described wells and the wells were rinsed once with DMEM. The keratinocyte buttons were implanted on the collagen carrier, immobilized with 3 μl of neutralized collagen (Vitrogen 1 mg/ml, neutralized with 10×PBS and 0.1M NaOH, pH 7.2) and incubated at 37° C. for 30 minutes. At the end of the incubation, 1 ml of keratinocyte serum free medium (SFM, Gibco/BRL Cat# 17005-042) was added to each well and the samples were incubated at 37° C. with 5% (v/v) $CO_2$. The medium was replaced every 3 days.

Keratinocyte outgrowth assays were conducted as follows: The culture media was removed from the wells by suctioning, and the samples were fixed in 3% (v/v) paraformaldehyde/PBS for 30 minutes at 22° C. The fixative was then removed from each well, and the samples were stained with 0.5% (w/v) Nile Blue Sulfate/1% (v/v) sulfuric acid/PBS for 1 hour at 37° C. The keratinocyte outgrowth was photographed with Polaroid 55 film.

EXAMPLE 9

Cell Proliferation and Matrix Binding Assays

The biological activity of solubilized recombinant $TGF\beta_1$-F1 was tested in a series of cell proliferation assays as described by Ikeda et al. (*Biochemistry* 26, 2406–2410, 1987, which is incorporated herein by reference) using Mink Lung epithelial (Mv1Lu) cells with minor modifications.

Mv1Lu cells were maintained in log-phase growth in Dulbecco's modified Eagles medium (DMEM; GIBCO) supplemented with 1% penicillin/streptomycin and 10% (v/v) fetal calf serum (FCS; GIBCO) at 37° C., 5% (v/v) $CO_2$ in humidified air. For cell proliferation assays, cells were seeded in 24-well plates (Costar) at a density of 1.5×10⁵ cells/well in normal growth medium. After an overnight incubation, the medium was replaced with 0.1% v/v FCS/DMEM. Serially diluted, renatured recombinant $TGF\beta_1$ fusion proteins were added to the wells and incubated for 24 hours. ³H-thymidine (1 μCi/well, specific activity 2 Ci/mmole, 74 GBq/mmole, ICN) was added during the last 4 hours of incubation. Human platelet-derived $TGF\beta_1$ (R & D Systems) was used as a standard and as a control. After incubation, the cells were precipitated twice with cold 10% (w/v) trichloroacetic acid (TCA), extracted with 0.2M NaOH, and neutralized with 0.5M acetic acid for analysis by liquid scintillation counting in cocktail.

Mv1Lu cells were also used to assess the biological activity of the recombinant $TGF\beta_1$-F1 fusion protein pre-absorbed onto collagen- and fibronectin-coated dishes. In these studies, 20 μl of pepsin-treated, acid-extracted bovine tendon collagen type I or human plasma fibronectin (20 μg/well; Telio) were dried onto each well of a 24-well plate (Costar) overnight. Following a brief ultraviolet light treatment to crosslink the matrix proteins, plates were counter-coated with 0.2% (w/v) bovine serum albumin (BSA). Serial dilutions of the recombinant $TGF\beta_1$-F1 were added to the coated wells in PBS and incubated at 37° C. for 2 hours. The wells were rinsed 3 times with DMEM, and Mv1Lu cells (1.5×10⁵ per well in 0.1% (v/v) FCS/DMEM) were added to each well. The cells were incubated for about 20 hours at 37° C., followed by quantification of ³H-thymidine incorporation into TCA-precipitable material as described above.

EXAMPLE 10

Collagen Binding Assay

Two different approaches were used to assess the affinity of the recombinant $TGF\beta_1$-F2 fusion protein for collagen and for gelatin.

In the first method, collagen and gelatin covalently conjugated to CNBr-activated Sephadex G-15 columns were used as test matrices. Preparations of native and denatured purified rat tail type I collagen were coupled onto CNBr-activated Sephadex G-15 beads. The beads were then washed extensively with 50 mM Tris buffer, pH 8, containing 1M NaCl. The fusion protein was applied to the medium in a buffered saline solution and was eluted with a linear salt gradient from 0.2 to 1M NaCl.

In the second method, the recombinant fusion protein was first immobilized onto Ni-NTA medium, then collagen (biosynthetically labeled with ³H-proline and purified from human fibroblast cultures) was applied to the Ni-NTA medium, and eluted with a linear gradient of either phosphate buffered NaCl (0.15 to 1.5M) or urea (0 to 4M).

Virtually, all of the recombinant growth factor bound to the collagen G-15 under these conditions, as determined by protein assays. Attempts to elute the bound protein from the collagen medium with a salt gradient or 2M urea were ineffective, suggesting that $TGF\beta_1$-F2 associates tightly with collagen. Similar results were obtained when $TGF\beta_1$-F2 was bound to a gelatin-Sephadex medium.

A different strategy was attempted in which the $TGF\beta_1$-F2 fusion protein was first immobilized on Ni-NTA medium and then exposed to biosynthetically-labeled ³H-collagen, which was loaded subsequently onto the medium. Under these conditions, a large portion of the radioactivity was found to bind to the medium. Washing the medium with a linear gradient of NaCl from 0.15 to 1.5M did not release the ³H-collagen. However, application of a urea gradient (0 to 4.0M) was able to quantitatively elute all bound radioactivity. In contrast, when the $TGF\beta_1$-F1 fusion protein, comprising the (His)₆ tag and the $TGF\beta_1$ active fragment, was applied to the Ni-NTA medium under identical conditions, very little ³H-collagen was retained on the medium, suggesting that the auxiliary collagen binding domain in $TGF\beta_1$-F2 afforded this high affinity interaction.

EXAMPLE 11

Stimulation of the Proliferation of NIH-3T3 Mouse Fibroblasts

The ability of $TGF\beta_1$-F1 and $TGF\beta_1$-F2 to stimulate the proliferation of NIH-3T3 mouse fibroblasts was assayed by plating NIH-3T3 mouse fibroblasts in 24 well plates at subconfluent densities (1.5×10⁵ cells/well) and culturing the cells for 48 hours in DMEM containing 0.5% (v/v) fetal calf serum. Commercial $TGF\beta_1$ or renatured $TGF\beta_1$-F2 samples were then added to each well and incubated for 18 hours prior to the addition of ³H-thymidine, followed by an additional 4 hours of incubation. To evaluate the effect of collagen-bound $TGF\beta_1$-F2 on the 3T3 fibroblasts, the fusion protein was first bound to collagen-coated wells. Cells (1.5×10⁵ cells/well) were seeded on top of the collagen with DMEM containing 0.5% (v/v) fetal calf serum or 0.5% (w/v) ITS (insulin, transferrin and selenium from Collaborative Biomedical Products, MA), harvested by trypsinization 72 hours later and quantified by direct counting.

As observed with human platelet TGFβ₁, TGFβ₁-F2 treatment of 3T3 fibroblasts for 18 hours following a 48-hour low serum starvation, resulted in a 30-fold increase in ³H-thymidine incorporation. When TGFβ₁-F2 was applied and bound to collagen-coated culture wells, and then cells were seeded on top of the TGFβ₁-F2/collagen in 0.5% (v/v) fetal calf serum/DMEM or ITS, no significant amount of stimulation of cell proliferation was observed, suggesting that the tight binding of TGFβ₁-F2 to collagen lowered the availability and/or the rate if release of the biologically active growth factor. By contrast, commercial TGFβ₁ absorbed onto collagen-coated wells stimulated the proliferation of 3T3 cells approximately fifteen fold.

EXAMPLE 12

Evaluation of TGFβ/Collagen Matrices in Wound Healing Models

The function of the fusion TGFβ were assessed in a series of classic bone healing models. Comparative studies utilizing the rat calvarial defect model in which a collagen matrix is used in the presence or absence of adsorbed TGFβ fusion proteins. The rate and extent of bone healing were evaluated by radiologic and histologic methods.

TGFβ₁ fusion protein was found to have a profound effect on bone healing in the rat calvarial defect model. The results demonstrated a marked stimulation of wound closure and osteogenesis at 2 and 4 weeks after surgery. In control rats, scar tissue formation was observed, whereas in the TGFβ₁ treated rats bone formation, rather than scar tissue was observed.

Histological examination of the tissue showed a marked recruitment of osteogenic precursors, a characteristic profile of cellular maturation and effective absorption of the original collagen matrix. By contrast, the collagen matrix alone (control) produced granulation tissue characterized by an infiltration of inflammatory cells. Quantification of calcium deposition in control versus TGFβ impregnated collagen matrices revealed significant improvements which were evident within 2 weeks. Angiogenesis was evident with TGFβ/collagen, as was a remarkable absence of adhesions between the newly formed bone and the underlying dura mater.

EXAMPLE 13

Development and Characterization of a Mesenchymal Stem Cell Trap

A diagram of wound healing stages observed within TGFβ treated collagen matrices depicts three major features: (I) recruitment and expansion of a mesenchymal stem cell (MSC) population, (II) elaboration (of factors) and differentiation of cellular phenotype, and (III) resolution and remodeling of the extracellular matrix (see FIG. 1).

Based on the magnitude and extent of precursor cell migration and proliferation observed in the rat calvarial model (Stage I), TGFβ impregnated collagen matrices were tested for their ability to selectively reinforce the proliferation of mesenchymal stem cells that are present in low abundance within human bone marrow aspirates under conditions that the remainder of the cellular components of the marrow would not survive.

Rescue and selection of TGFβ Responsive stem cells from human bone marrow aspirates upon 15 days of serum deprivation was observed.

EXAMPLE 14

2-Stage Histogenesis of Human "Artificial Skin" on Collagen Supports

Collagen matrices and sheets, though optimal in terms of structural integrity and biodegradability, can cause inflammatory responses (rejection) and fibrosis (scarring). By contrast, TGFβ impregnated collagen matrices inhibit inflammatory processes while promoting angiogenesis and histogenesis. TGFβ is a natural and critical component regulating epithelial-mesenchymal interactions in the developmental morphogenesis of skin appendages. Collagen bound TGFβ₁-F2 fusion proteins can function effectively to select and expand (capture) a population of mesenchymal stem cells in vitro.

The development of an autologous "artificial" skin is feasible. The experimental procedure is to select and expand a population of explanted human fibroblasts, along with other resident mesenchymal precursors, within TGFβ impregnated collagen sheets. This procedure is continued in vitro up to an optimized point whereby the collagen sheet is effectively cellularized yet not degraded. At or just prior to this point, the collagen/connective tissue sheet is epithelialized by the application of an explanted plug of keratinocytes.

The human artificial skin comprised of TGFβ impregnated collagen sheets which have been cellularized and epithelialized in a 2-Stage approach is evaluated histologically and, once experimental conditions have been optimized, the "skin" is tested in a nude mouse wound healing model.

In these animal models, several considerations and critical parameters will be evaluated, as follows: Comparative studies are performed to evaluate the outcome and scar formation involving TGFβ/collagen sheets cultured under high serum conditions (mostly fibroblastic cells) versus TGFβ/collagen sheets in which the population of pluripotent mesenchymal stem cells have been selected and expanded by culture under low serum conditions.

Such studies are expected to result in an enrichment (recruitment and expansion) of pluripotent stem cells will facilitate normal histogenesis and wound healing. The application of recombinant TGFβ fusion proteins, including collagen-binding (F2) and fibronectin-binding (F3) constructs, to the cellularized "skin" (i.e., cellularized/ epithelialized collagen sheets) and/or the wound surface is evaluated in terms of efficacy in promoting adherence, angiogenesis, and histogenesis. Such studies are also expected to result in a secondary application of TGFβ fusion proteins which will retard rejection and promote fusion of cultured tissues. The timing of each stage of the ex vivo - tissue culture, as well as the thickness and physicochemistry of the collagen sheets, is also assessed.

EXAMPLE 15

The use of TGF-β as a Wound Healing Enhancing Agent

TGFβ is known to effect wound healing by modulating stem cells proliferation and the expression of specific genes including those encoding for extracellular matrix proteins and cellular receptors. Numerous studies using animal models have demonstrated the potential of TGFβ to promote wound healing. TGFβ of the present invention exhibits biological activity and its use, in place of the naturally occurring TGFβ, allows the treatment of many conditions which previously have been considered as only potential clinical applications, due to the limited availability of TGFβ. Regeneration of the skeleton It has been found that injections of TGFβ₁ on the periosteal layer stimulated bone formation in newborn rats. Different dosages of TGFβ added to demineralized bone matrix paste, formed into cylinders and implanted onto the periosteum of rabbits have shown that TGFβ induced higher levels of (accelerated) trabecular bone formation than controls. TGFβ also caused greater resorption of the demineralized bone. It has also been shown that a single application of TGFβ$_1$ in a simple 3% methylcellulose gel to large skull defects in rabbits was able to induce intramembranous bone formation and complete bony bridging of defects was observed within 28 days after treatment with 2 μg of TGFβ. In neonatal rats, 12-day treatment of TGFβ$_1$ injection onto the outer periostea of the right side of the parietal bone increased the number of osteoprogenitor cells, resulting in intramembranous ossification. In adult rats, TGFβ$_1$ induced differentiation of chondrocytes. Cartilage masses were found to be surrounded by mesenchymal cells. In these animals the cartilage matrix was partially calcified, with chondrocytes buried therein. Marrow cavities containing some multinuclear osteoblasts were also observed in the calcified matrix. These findings indicate that TGFβ$_1$ stimulated the differentiation of mesenchymal cells into chondrocytes and produced cartilaginous matrix. TGFβ$_1$ induced intramembranous ossification of the parietal bone in neonatal rats, and it induced endochondral ossification in adults. These results show different responses of mesenchymal cells in the periosteum to TGFβ$_1$ which may depend on the age of the animals used; namely, they may reflect the respective osteogenic stages of modeling and remodeling.

It has also been shown, that TGFβ counteracts the deleterious effects of interleukin-1 (IL-1) on articular cartilage proteoglycan synthesis and content indicating that TGFβ plays an important role in articular cartilage restoration after IL-1 induced proteoglycan depletion. It has also been demonstrated that short term systemic injection of recombinant TGFβ$_2$ increases cancellous bone formation rate in juvenile and adult rats. It has also been shown that continuous local application of TGFβ for 6 weeks enhances fracture healing of tibial defects in rabbits. Similarly, it has been shown that local injection of TGFβ at the site of tibial fractures induced a dose-dependent increase in the cross-sectional area of the callus and bone at the fracture line.

Skin wound healing

The treatment of incisional wounds of rats, which received total body radiation, with a single dose of TGFβ$_1$ (2 μg/wound) using 3% methylcellulose as a delivery vehicle, resulted in a significant acceleration of soft tissue repair and wound-breaking strength in the absence of monocytes and macrophages. TGFβ$_1$ was not able to reverse healing deficit in the megavoltage electron beam surface irradiated skin wounds. The treatment of partial-thickness wounds in pigs topically with TGFβ using Silvadene cream (Marion Labs, Kansas, Mo.) as a vehicle was shown to accelerate the regeneration of dermis. It has also been shown that TGFβ accelerated the maturation of a neo-vascularized skin flap in rabbits.

Protection and rescue from impaired wound healing

It has been shown that mice which received TGFβ prior to treatment of high doses of 5-fluro-uracil exhibited a hematologic recovery and were preferentially rescued by a suboptimal number of transplanted bone marrow cells. It was also shown that pretreatment of mice with TGFβ protected 70–80% of them from lethal doses of the noncycle active chemotherapeutic drug, doxorubicin hydrochloride (DXR). It has also been found that parenteral steroids (β-methasone, 12 mg/50 g injected intramuscularly twice daily) induced an impairment of breaking load on a healed longitudinal intestinal wound in pigs. TGFβ in a collagen suspension was used to treat these wounds and was found to reverse the effect of the steroids and significantly strengthened these wounds.

Other studies have been directed at the effect of TGFβ on an Adriamycin-impaired wound healing model. In this model, a systemic adriamycin injection (8 mg/kg) produces significant decreases in wound tear strength and wound tear energy when compared with that of normal rats at seven and 10 days. A single dose of TGFβ (2 μg) in a collagen vehicle was shown to stimulate a reversal of this wound healing impairment at day 10. Similarly, intravenously administered TGFβ at 100–500 mg/kg dosage can reverse age- or glucocorticoid-impaired healing of incisional wounds. Treatment of experimental allergic encephalomyelitis (EAE) with TGFβ$_2$ resulted in the inhibition of T-cell activation and proliferation in vitro. Long-term treatment was effective in reducing clinical severity of EAE suggesting a potential use of TGFβ$_2$ as a therapeutic agent for human demyelinating diseases such as multiple sclerosis.

Protection against myocardial dysfunction and stroke

It has been shown that TGFα reduces endothelial cell release of nitric oxide, while TGFβ appears to protect against myocardial dysfunction induced by prolonged ischemia and reperfusion probably by reducing plasma TGFα levels, blocking neutrophil adherence, and promoting nitric oxide release.

Other studies have been directed at the effect of TGFβ on thromboembolic stroke in a rabbit model. An autologous clot embolus was introduced intracranially through the right internal carotid artery of rabbits to induce a thromboembolic stroke. TGFβ in an albumin vehicle was administered as an intracarotid bolus immediately before autologous clot embolization. The results showed treatment with 10 and 50 μg TGFβ reduced the infarct size and there was a greater return of cerebral blood flow in the first 2 hours after embolization. Other studies have addressed the ability of TGF to preserve endothelial functions of coronary arteries in dogs by infusing TGF into the left anterior descending coronary artery distal to the site subjected to multiple brief occlusions and reperfusion. TGFβ$_1$ prevented impaired endothelium-dependent relaxation after multiple brief occlusions and reperfussions suggesting that TGFβ$_1$ can play a protective role in the endothelial injury induced by repeated episodes of coronary artery occlusion and reperfusion.

Immune suppression

It has also been shown that prolonged survival of cardiac graft transplants can be achieved by injecting plasmid DNA encoding TGF under the control of SV40 promoter into grafts from syngeneic or allogenic donors prior to implantation into recipients. In other studies in mice, the intramuscular injection of a vector encoding TGFβ$_1$ depressed the anti-transferrin antibody response and caused an 8-fold increase in plasma TGFβ$_1$ activity. The TGFβ$_1$ plasmid injection induced biological effects characteristic of TGFβ in regulating humoral and cellular immune responses in vivo but did not cause muscle infiltration with monocytes or neutrophils and there was no evidence for fibrotic changes.

Applications for humans currently under clinical trials

Other studies have shown in a randomized multicenter clinical study of patients with full-thickness macular holes, that 0.66 pg of TGFβ$_2$, applied locally, to be successful in flattening the rim of subretinal fluid surrounding macular holes. The study further showed that TGFβ$_2$ retreatment (1.33 pg) on full-thickness macular holes which failed to close after vitreous surgery appeared to have a beneficial effect on both neurosensory retinal flattening and visual outcome.

Pharmacokinetics of TGFβ

Other studies have included a detailed pharmacokinetic and tissue distribution study of TGF as a potential intravenous bolus or topical wound healing enhancing agent. It has been found that the half-life of topically administered TGF has a plasma half-life ranging between 61 to 163 minutes depending on the dose and duration of the treatment. Other studies have shown that $^{125}$I TGF was detectable 16 days after a single dose of TGF, formulated in a 3% methylcellulose vehicle, in the rabbit calvarial defect model. It has also been demonstrated that high-dose dermal application of TGF resulted in local effects attributed to known biological activities of TGFβ at the wound sites without systemic toxicity.

EXAMPLE 16

Methods of Delivery of TGF-β

Systemic injection

A suitable method to administer TGFβ is injection of the growth factor in a liquid vehicle.

Injection of DNA vector

Plasmid DNA encoding the human TGFβ$_1$ under the control of a known promoter can be injected intramuscularly.

Topical application

Silvadene cream (36% methylcellulose) and soluble collagen are useful as vehicles in topical or local administration of TGFβ.

Implantable solid phase carriers

TGFβ (1 to 10 μg) enclosed in a gelatin capsule containing methylcellulose can be implanted into surgical chambers and in bone to increased bone formation. Biodegradable controlled release systems for TGFβ$_1$ which comprise poly (DL-lactic-co-glycolic acid) (PLPG) and demineralized bone matrix (DBM) can be used. DBM alone, 3% methylcellulose gel, and alginate beads are also effective carriers for TGFβ.

The present invention is not to be limited to the specific embodiments which are shown or described above and which are merely illustrative. Various and numerous other arrangements and applications may be devised by one skilled in the art without departing from the spirit and scope of this invention. For example, one skilled in the art will be aware that the DNA sequences can be changed without changing the amino acid sequence of the proteins encoded or that the DNA can be changed to change the amino acid specified at a particular place in a polypeptide, but which do not change the functional properties of the polypeptide produced from the DNA sequence, i.e. conservative substitutions. Such modified DNA sequences and amino acid sequences are considered to be included within the scope of the present invention.

The scope of the invention is defined in the following claims.

---

What is claimed is:

1. An artificial skin made by the process comprising:
   impregnating a collagen matrix with transforming growth factor-β comprising a collagen-binding site to thereby bind the transforming growth factor-β to the collagen matrix;
   incubating the impregnated matrix with a source of fibroblasts and mesenchymal stem cells to form a captured population of mesenchymal stem cells, within the impregnated matrix; and
   incubating the captured population of mesenchymal stem cells with a source of keratinocytes which epithelialize the collagen matrix to thereby form an artificial skin.

2. An artificial skin as recited in claim 1 wherein the collagen matrix comprises a collagen sheet.

3. An artificial skin as recited in claim 1 wherein the mesenchymal stem cells are derived from an intended recipient of the artificial skin.

4. An artificial skin as recited in claim 1 wherein the transforming growth factor-β is selected from the group consisting of transforming growth factor-β₁, transforming growth factor-β₂ and transforming growth factor-β₃.

5. An artificial skin as recited in claim 1 wherein the transforming growth factor-β is a fusion protein.

6. An artificial skin as recited in claim 5 wherein the fusion protein comprises a purification tag.

7. An artificial skin as recited in claim 5 wherein the fusion protein comprises at least one proteinase site.

8. An artificial skin as recited in claim 5 wherein the fusion protein comprises an extracellular matrix binding site.

9. An artificial skin as recited in claim 8 wherein the extracellular binding site binds fibronectin or cell surface.

10. An artificial skin as recited in claim 5 wherein the fusion protein comprises a transforming growth factor active fragment.

11. An artificial skin comprising:
    a collagen matrix impregnated with transforming growth factor-β comprising a collagen-binding site to thereby bind the transforming growth factor-β to the collagen matrix;
    fibroblasts and mesenchymal cells captured within the impregnated collagen matrix; and
    keratinocytes epithelialized onto the collagen matrix to thereby form an artificial skin.

12. An artificial skin as recited in claim 11 wherein the collagen matrix comprises a collagen sheet.

13. An artificial skin as recited in claim 11 wherein the mesenchymal cells are derived from an intended recipient of the artificial skin.

14. An artificial skin as recited in claim 11 wherein the transforming growth factor-β is selected from the group consisting of transforming growth factor-β₁, transforming growth factor-β₂ and transforming growth factor-β₃.

15. An artificial skin as recited in claim 11 wherein the transforming growth factor-β is a fusion protein.

16. An artificial skin as recited in claim 15 wherein the fusion protein comprises a purification tag.

17. An artificial skin as recited in claim 15 wherein the fusion protein comprises at least one proteinase site.

18. An artificial skin as recited in claim 15 wherein the fusion protein comprises an extracellular matrix binding site.

19. An artificial skin as recited in claim 18 wherein the extracellular binding site binds fibronectin or cell surface.

20. An artificial skin as recited in claim 15 wherein the fusion protein comprises a transforming growth factor active fragment.

* * * * *

SEQUENCE LISTING ( 1 ) GENERAL INFORMATION:

( i i i ) NUMBER OF SEQUENCES: 34

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

His  Asp  Val  Leu  Lys
 1                          5

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:2:

Leu  Leu  Val  Tyr
 1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:3:

Ala Ala Pro Phe
1

( 2 ) INFORMATION FOR SEQ ID NO:4:

( i ) SEQUENCE CHARACTERISTICS:
                ( A ) LENGTH: 3 amino acids
                ( B ) TYPE: amino acid
                ( C ) STRANDEDNESS:
                ( D ) TOPOLOGY: linear ( i i ) MOLECULE TYPE: peptide ( x i ) SEQUENCE DESCRIPTION: SEQ ID NO:4:

Ala Pro Ala
1

( 2 ) INFORMATION FOR SEQ ID NO:5:

( i ) SEQUENCE CHARACTERISTICS:
                ( A ) LENGTH: 3 amino acids
                ( B ) TYPE: amino acid
                ( C ) STRANDEDNESS:
                ( D ) TOPOLOGY: linear ( i i ) MOLECULE TYPE: peptide ( x i ) SEQUENCE DESCRIPTION: SEQ ID NO:5:

Ala Ala Ala
1

( 2 ) INFORMATION FOR SEQ ID NO:6:

( i ) SEQUENCE CHARACTERISTICS:
                ( A ) LENGTH: 2 amino acids
                ( B ) TYPE: amino acid
                ( C ) STRANDEDNESS:
                ( D ) TOPOLOGY: linear ( i i ) MOLECULE TYPE: peptide ( x i ) SEQUENCE DESCRIPTION: SEQ ID NO:6:

Gly Arg
1

( 2 ) INFORMATION FOR SEQ ID NO:7:

( i ) SEQUENCE CHARACTERISTICS:
                ( A ) LENGTH: 3 amino acids
                ( B ) TYPE: amino acid
                ( C ) STRANDEDNESS:
                ( D ) TOPOLOGY: linear ( i i ) MOLECULE TYPE: peptide ( x i ) SEQUENCE DESCRIPTION: SEQ ID NO:7:

Leu Thr Arg
1

( 2 ) INFORMATION FOR SEQ ID NO:8:

( i ) SEQUENCE CHARACTERISTICS:
                ( A ) LENGTH: 7 amino acids
                ( B ) TYPE: amino acid
                ( C ) STRANDEDNESS:
                ( D ) TOPOLOGY: linear ( i i ) MOLECULE TYPE: peptide ( x i ) SEQUENCE DESCRIPTION: SEQ ID NO:8:

Pro Ile Glu Phe Phe Arg Leu
 1               5

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:9:

Lys Pro Ala Lys Phe Phe Arg
 1               5

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:10:

Leu Ser Phe Leu Ala Leu
 1               5

( 2 ) INFORMATION FOR SEQ ID NO:11:

( i ) SEQUENCE CHARACTERISTICS:
        ( A ) LENGTH: 3 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:11:

Ala Ala Phe
 1

( 2 ) INFORMATION FOR SEQ ID NO:12:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..12

( i x ) FEATURE:
        ( A ) NAME/KEY: mat_peptide
        ( B ) LOCATION: 1

( x i ) SEQUENCE DESCRIPTION: SEQ ID NO:12:

ATC GAA GGT CGT                                                                      12
Ile Glu Gly Leu
 1

( 2 ) INFORMATION FOR SEQ ID NO:13:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:13:

```
Ile  Glu  Gly  Leu
 1
```

( 2 ) INFORMATION FOR SEQ ID NO:14:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..18

( i x ) FEATURE:
        ( A ) NAME/KEY: mat_peptide
        ( B ) LOCATION: 1

( x i ) SEQUENCE DESCRIPTION: SEQ ID NO:14:

```
CTG  GTT  CCG  CGT  GGA  TCC                                    18
Leu  Val  Pro  Arg  Gly  Ser
 1                     5
```

( 2 ) INFORMATION FOR SEQ ID NO:15:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:15:

```
Leu  Val  Pro  Arg  Gly  Ser
 1                     5
```

( 2 ) INFORMATION FOR SEQ ID NO:16:

( i ) SEQUENCE CHARACTERISTICS:
        ( A ) LENGTH: 3 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:16:

```
Arg  Gly  Asp
 1
```

( 2 ) INFORMATION FOR SEQ ID NO:17:

( i ) SEQUENCE CHARACTERISTICS:
        ( A ) LENGTH: 18 base pairs
        ( B ) TYPE: nucleic acid -continued

```
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..18

( i x ) FEATURE:
        ( A ) NAME/KEY: mat_peptide
        ( B ) LOCATION: 1

( x i ) SEQUENCE DESCRIPTION: SEQ ID NO:17:

GGT  GGC  TGG  AGC  CAC  TGG                                                  18
Gly  Gly  Trp  Ser  His  Trp
 1                  5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

Gly  Gly  Trp  Ser  His  Trp
 1                  5

( 2 ) INFORMATION FOR SEQ ID NO:19:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..27

( i x ) FEATURE:
        ( A ) NAME/KEY: mat_peptide
        ( B ) LOCATION: 1

( x i ) SEQUENCE DESCRIPTION: SEQ ID NO:19:

TGG  CGC  GAA  CCG  AGC  TTC  ATG  GCT  CTG                                   27
Trp  Arg  Glu  Pro  Ser  Phe  Met  Ala  Leu
 1                  5

( 2 ) INFORMATION FOR SEQ ID NO:20:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

Trp  Arg  Glu  Pro  Ser  Phe  Met  Ala  Leu
 1                  5

( 2 ) INFORMATION FOR SEQ ID NO:21:

( i ) SEQUENCE CHARACTERISTICS:
        ( A ) LENGTH: 18 base pairs
        ( B ) TYPE: nucleic acid
```

( C ) STRANDEDNESS: single
           ( D ) TOPOLOGY: linear ( i i ) MOLECULE TYPE: cDNA ( i x ) FEATURE:
           ( A ) NAME/KEY: CDS
           ( B ) LOCATION: 1..18

( i x ) FEATURE:
           ( A ) NAME/KEY: mat_peptide
           ( B ) LOCATION: 1

( x i ) SEQUENCE DESCRIPTION: SEQ ID NO:21:

```
CAT  CAT  CAT  CAT  CAT  CAC                                                       18
His  His  His  His  His  His
 1                  5
```

( 2 ) INFORMATION FOR SEQ ID NO:22:

( i ) SEQUENCE CHARACTERISTICS:
           ( A ) LENGTH: 6 amino acids
           ( B ) TYPE: amino acid
           ( D ) TOPOLOGY: linear ( i i ) MOLECULE TYPE: protein ( x i ) SEQUENCE DESCRIPTION: SEQ ID NO:22:

```
His  His  His  His  His  His
 1                  5
```

( 2 ) INFORMATION FOR SEQ ID NO:23:

( i ) SEQUENCE CHARACTERISTICS:
           ( A ) LENGTH: 45 base pairs
           ( B ) TYPE: nucleic acid
           ( C ) STRANDEDNESS: single
           ( D ) TOPOLOGY: linear ( i i ) MOLECULE TYPE: cDNA ( i x ) FEATURE:
           ( A ) NAME/KEY: CDS
           ( B ) LOCATION: 1..45

( i x ) FEATURE:
           ( A ) NAME/KEY: mat_peptide
           ( B ) LOCATION: 1

( x i ) SEQUENCE DESCRIPTION: SEQ ID NO:23:

```
AAA  GAA  ACC  GCT  GCT  GCT  AAA  TTC  GAA  CGC  CAG  CAC  ATG  GAC  AGC         45
Lys  Glu  Thr  Ala  Ala  Ala  Lys  Phe  Glu  Arg  Gln  His  Met  Asp  Ser
 1                  5                            10                 15
```

( 2 ) INFORMATION FOR SEQ ID NO:24:

( i ) SEQUENCE CHARACTERISTICS:
           ( A ) LENGTH: 15 amino acids
           ( B ) TYPE: amino acid
           ( D ) TOPOLOGY: linear ( i i ) MOLECULE TYPE: protein ( x i ) SEQUENCE DESCRIPTION: SEQ ID NO:24:

```
Lys  Glu  Thr  Ala  Ala  Ala  Lys  Phe  Glu  Arg  Gln  His  Met  Asp  Ser
 1                  5                            10                 15
```

( 2 ) INFORMATION FOR SEQ ID NO:25:

( i ) SEQUENCE CHARACTERISTICS:
           ( A ) LENGTH: 654 base pairs
           ( B ) TYPE: nucleic acid (C) STRANDEDNESS: double
(D) TOPOLOGY: linear (ii) MOLECULE TYPE: cDNA (ix) FEATURE:
(A) NAME/KEY: CDS
(B) LOCATION: 1..654

(ix) FEATURE:
(A) NAME/KEY: mat_peptide
(B) LOCATION: 1

(xi) SEQUENCE DESCRIPTION: SEQ ID NO:25:

| ATG | TCC | CCT | ATA | CTA | GGT | TAT | TGG | AAA | ATT | AAG | GGC | CTT | GTG | CAA | CCC | 48 |
| Met | Ser | Pro | Ile | Leu | Gly | Tyr | Trp | Lys | Ile | Lys | Gly | Leu | Val | Gln | Pro | |
| 1 | | | | 5 | | | | | 10 | | | | | 15 | | |

| ACT | CGA | CTT | CTT | TTG | GAA | TAT | CTT | GAA | GAA | AAA | TAT | GAA | GAG | CAT | TTG | 96 |
| Thr | Arg | Leu | Leu | Leu | Glu | Tyr | Leu | Glu | Glu | Lys | Tyr | Glu | Glu | His | Leu | |
| | | | 20 | | | | | 25 | | | | | 30 | | | |

| TAT | GAG | CGC | GAT | GAA | GGT | GAT | AAA | TGG | CGA | AAC | AAA | AAG | TTT | GAA | TTG | 144 |
| Tyr | Glu | Arg | Asp | Glu | Gly | Asp | Lys | Trp | Arg | Asn | Lys | Lys | Phe | Glu | Leu | |
| | | 35 | | | | | 40 | | | | | 45 | | | | |

| GGT | TTG | GAG | TTT | CCC | AAT | CTT | CCT | TAT | TAT | ATT | GAT | GGT | GAT | GTT | AAA | 192 |
| Gly | Leu | Glu | Phe | Pro | Asn | Leu | Pro | Tyr | Tyr | Ile | Asp | Gly | Asp | Val | Lys | |
| | 50 | | | | | 55 | | | | | 60 | | | | | |

| TTA | ACA | CAG | TCT | ATG | GCC | ATC | ATA | CGT | TAT | ATA | GCT | GAC | AAG | CAC | AAC | 240 |
| Leu | Thr | Gln | Ser | Met | Ala | Ile | Ile | Arg | Tyr | Ile | Ala | Asp | Lys | His | Asn | |
| 65 | | | | 70 | | | | | 75 | | | | | 80 | | |

| ATG | TTG | GGT | GGT | TGT | CCA | AAA | GAG | CGT | GCA | GAG | ATT | TCA | ATG | CTT | GAA | 288 |
| Met | Leu | Gly | Gly | Cys | Pro | Lys | Glu | Arg | Ala | Glu | Ile | Ser | Met | Leu | Glu | |
| | | | | 85 | | | | | 90 | | | | | 95 | | |

| GGA | GCG | GTT | TTG | GAT | ATT | AGA | TAC | GGT | GTT | TCG | AGA | ATT | GCA | TAT | AGT | 336 |
| Gly | Ala | Val | Leu | Asp | Ile | Arg | Tyr | Gly | Val | Ser | Arg | Ile | Ala | Tyr | Ser | |
| | | | 100 | | | | | 105 | | | | | 110 | | | |

| AAA | GAC | TTT | GAA | ACT | CTC | AAA | GTT | GAT | TTT | CTT | AGC | AAG | CTA | CCT | GAA | 384 |
| Lys | Asp | Phe | Glu | Thr | Leu | Lys | Val | Asp | Phe | Leu | Ser | Lys | Leu | Pro | Glu | |
| | | 115 | | | | | 120 | | | | | 125 | | | | |

| ATG | CTG | AAA | ATG | TTC | GAA | GAT | CGT | TTA | TGT | CAT | AAA | ACA | TAT | TTA | AAT | 432 |
| Met | Leu | Lys | Met | Phe | Glu | Asp | Arg | Leu | Cys | His | Lys | Thr | Tyr | Leu | Asn | |
| | 130 | | | | | 135 | | | | | 140 | | | | | |

| GGT | GAT | CAT | GTA | ACC | CAT | CCT | GAC | TTC | ATG | TTG | TAT | GAC | GCT | CTT | GAT | 480 |
| Gly | Asp | His | Val | Thr | His | Pro | Asp | Phe | Met | Leu | Tyr | Asp | Ala | Leu | Asp | |
| 145 | | | | 150 | | | | | 155 | | | | | 160 | | |

| GTT | GTT | TTA | TAC | ATG | GAC | CCA | ATG | TGC | CTG | GAT | GCG | TTC | CCA | AAA | TTA | 528 |
| Val | Val | Leu | Tyr | Met | Asp | Pro | Met | Cys | Leu | Asp | Ala | Phe | Pro | Lys | Leu | |
| | | | | 165 | | | | | 170 | | | | | 175 | | |

| GTT | TGT | TTT | AAA | AAA | CGT | ATT | GAA | GCT | ATC | CCA | CAA | ATT | GAT | AAG | TAC | 576 |
| Val | Cys | Phe | Lys | Lys | Arg | Ile | Glu | Ala | Ile | Pro | Gln | Ile | Asp | Lys | Tyr | |
| | | | 180 | | | | | 185 | | | | | 190 | | | |

| TTG | AAA | TCC | AGC | AAG | TAT | ATA | GCA | TGG | CCT | TTG | CAG | GGC | TGG | CAA | GCC | 624 |
| Leu | Lys | Ser | Ser | Lys | Tyr | Ile | Ala | Trp | Pro | Leu | Gln | Gly | Trp | Gln | Ala | |
| | | | 195 | | | | | 200 | | | | | 205 | | | |

| ACG | TTT | GGT | GGT | GGC | GAC | CAT | CCT | CCA | AAA | | | | | | | 654 |
| Thr | Phe | Gly | Gly | Gly | Asp | His | Pro | Pro | Lys | | | | | | | |
| | 210 | | | | | 215 | | | | | | | | | | |

(2) INFORMATION FOR SEQ ID NO:26:

(i) SEQUENCE CHARACTERISTICS:
(A) LENGTH: 218 amino acids
(B) TYPE: amino acid
(D) TOPOLOGY: linear (ii) MOLECULE TYPE: protein ( x i ) SEQUENCE DESCRIPTION: SEQ ID NO:26:

| Met | Ser | Pro | Ile | Leu | Gly | Tyr | Trp | Lys | Ile | Lys | Gly | Leu | Val | Gln | Pro |
|---|---|---|---|---|---|---|---|---|---|---|---|---|---|---|---|
| 1 | | | | 5 | | | | | 10 | | | | | 15 | |

| Thr | Arg | Leu | Leu | Leu | Glu | Tyr | Leu | Glu | Glu | Lys | Tyr | Glu | Glu | His | Leu |
|---|---|---|---|---|---|---|---|---|---|---|---|---|---|---|---|
| | | | 20 | | | | | 25 | | | | | 30 | | |

| Tyr | Glu | Arg | Asp | Glu | Gly | Asp | Lys | Trp | Arg | Asn | Lys | Lys | Phe | Glu | Leu |
|---|---|---|---|---|---|---|---|---|---|---|---|---|---|---|---|
| | | 35 | | | | | 40 | | | | | 45 | | | |

| Gly | Leu | Glu | Phe | Pro | Asn | Leu | Pro | Tyr | Tyr | Ile | Asp | Gly | Asp | Val | Lys |
|---|---|---|---|---|---|---|---|---|---|---|---|---|---|---|---|
| | 50 | | | | | 55 | | | | | 60 | | | | |

| Leu | Thr | Gln | Ser | Met | Ala | Ile | Ile | Arg | Tyr | Ile | Ala | Asp | Lys | His | Asn |
|---|---|---|---|---|---|---|---|---|---|---|---|---|---|---|---|
| 65 | | | | | 70 | | | | | 75 | | | | | 80 |

| Met | Leu | Gly | Gly | Cys | Pro | Lys | Glu | Arg | Ala | Glu | Ile | Ser | Met | Leu | Glu |
|---|---|---|---|---|---|---|---|---|---|---|---|---|---|---|---|
| | | | | 85 | | | | | 90 | | | | | 95 | |

| Gly | Ala | Val | Leu | Asp | Ile | Arg | Tyr | Gly | Val | Ser | Arg | Ile | Ala | Tyr | Ser |
|---|---|---|---|---|---|---|---|---|---|---|---|---|---|---|---|
| | | | 100 | | | | | 105 | | | | | 110 | | |

| Lys | Asp | Phe | Glu | Thr | Leu | Lys | Val | Asp | Phe | Leu | Ser | Lys | Leu | Pro | Glu |
|---|---|---|---|---|---|---|---|---|---|---|---|---|---|---|---|
| | | 115 | | | | | 120 | | | | | 125 | | | |

| Met | Leu | Lys | Met | Phe | Glu | Asp | Arg | Leu | Cys | His | Lys | Thr | Tyr | Leu | Asn |
|---|---|---|---|---|---|---|---|---|---|---|---|---|---|---|---|
| | 130 | | | | | 135 | | | | | 140 | | | | |

| Gly | Asp | His | Val | Thr | His | Pro | Asp | Phe | Met | Leu | Tyr | Asp | Ala | Leu | Asp |
|---|---|---|---|---|---|---|---|---|---|---|---|---|---|---|---|
| 145 | | | | | 150 | | | | | 155 | | | | | 160 |

| Val | Val | Leu | Tyr | Met | Asp | Pro | Met | Cys | Leu | Asp | Ala | Phe | Pro | Lys | Leu |
|---|---|---|---|---|---|---|---|---|---|---|---|---|---|---|---|
| | | | | 165 | | | | | 170 | | | | | 175 | |

| Val | Cys | Phe | Lys | Lys | Arg | Ile | Glu | Ala | Ile | Pro | Gln | Ile | Asp | Lys | Tyr |
|---|---|---|---|---|---|---|---|---|---|---|---|---|---|---|---|
| | | | 180 | | | | | 185 | | | | | 190 | | |

| Leu | Lys | Ser | Ser | Lys | Tyr | Ile | Ala | Trp | Pro | Leu | Gln | Gly | Trp | Gln | Ala |
|---|---|---|---|---|---|---|---|---|---|---|---|---|---|---|---|
| | | 195 | | | | | 200 | | | | | 205 | | | |

| Thr | Phe | Gly | Gly | Gly | Asp | His | Pro | Pro | Lys |
|---|---|---|---|---|---|---|---|---|---|
| | 210 | | | | | 215 | | | |

( 2 ) INFORMATION FOR SEQ ID NO:27:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..27

( i x ) FEATURE:
        ( A ) NAME/KEY: mat_peptide
        ( B ) LOCATION: 1

( x i ) SEQUENCE DESCRIPTION: SEQ ID NO:27:

| TAC | CCA | TAC | GAT | GTT | CCA | GAT | TAC | GCT | 27 |
|---|---|---|---|---|---|---|---|---|---|
| Tyr | Pro | Tyr | Asp | Val | Pro | Asp | Tyr | Ala | |
| 1 | | | | 5 | | | | | |

( 2 ) INFORMATION FOR SEQ ID NO:28:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

Tyr Pro Tyr Asp Val Pro Asp Tyr Ala
 1               5

( 2 ) INFORMATION FOR SEQ ID NO:29:

( i ) SEQUENCE CHARACTERISTICS:
         ( A ) LENGTH: 339 base pairs
         ( B ) TYPE: nucleic acid
         ( C ) STRANDEDNESS: double
         ( D ) TOPOLOGY: linear ( i i ) MOLECULE TYPE: cDNA ( i x ) FEATURE:
         ( A ) NAME/KEY: CDS
         ( B ) LOCATION: 1..333

( i x ) FEATURE:
         ( A ) NAME/KEY: CDS
         ( B ) LOCATION: 1..336

( i x ) FEATURE:
         ( A ) NAME/KEY: mat_peptide
         ( B ) LOCATION: 1

( x i ) SEQUENCE DESCRIPTION: SEQ ID NO:29:

| GCC | CTG | GAC | ACC | AAC | TAT | TGC | TTC | AGC | TCC | ACG | GAG | AAG | AAC | TGC | TGC | 48 |
| Ala | Leu | Asp | Thr | Asn | Tyr | Cys | Phe | Ser | Ser | Thr | Glu | Lys | Asn | Cys | Cys | |
| 1 | | | | 5 | | | | | 10 | | | | | 15 | | |

| GTG | CGG | CAG | CTG | TAC | ATT | GAC | TTC | CGC | AAG | GAC | CTC | GGC | TGG | AAG | TGG | 96 |
| Val | Arg | Gln | Leu | Tyr | Ile | Asp | Phe | Arg | Lys | Asp | Leu | Gly | Trp | Lys | Trp | |
| | | | 20 | | | | | 25 | | | | | 30 | | | |

| ATC | CAT | GAG | CCC | AAG | GGC | TAC | CAT | GCC | AAC | TTC | TGC | CTC | GGG | CCC | TGC | 144 |
| Ile | His | Glu | Pro | Lys | Gly | Tyr | His | Ala | Asn | Phe | Cys | Leu | Gly | Pro | Cys | |
| | | 35 | | | | | 40 | | | | | 45 | | | | |

| CCC | TAC | ATT | TGG | AGC | CTG | GAC | ACG | CAG | TAC | AGC | AAG | GTC | CTG | GCC | CTG | 192 |
| Pro | Tyr | Ile | Trp | Ser | Leu | Asp | Thr | Gln | Tyr | Ser | Lys | Val | Leu | Ala | Leu | |
| | | 50 | | | | | 55 | | | | | 60 | | | | |

| TAC | AAC | CAG | CAT | AAC | CCG | GGC | GCC | TCG | GCG | GCG | CCG | TGC | TGC | GTG | CCG | 240 |
| Tyr | Asn | Gln | His | Asn | Pro | Gly | Ala | Ser | Ala | Ala | Pro | Cys | Cys | Val | Pro | |
| 65 | | | | | 70 | | | | | 75 | | | | | 80 | |

| CAG | GCG | CTG | GAG | CCG | CTG | CCC | ATC | GTG | TAC | TAC | GTG | GGC | CGC | AAG | CCC | 288 |
| Gln | Ala | Leu | Glu | Pro | Leu | Pro | Ile | Val | Tyr | Tyr | Val | Gly | Arg | Lys | Pro | |
| | | | | 85 | | | | | 90 | | | | | 95 | | |

| AAG | GTG | GAG | CAG | CTG | TCC | AAC | ATG | ATC | GTG | CGC | TCC | TGC | AAG | TGC | AGC | 336 |
| Lys | Val | Glu | Gln | Leu | Ser | Asn | Met | Ile | Val | Arg | Ser | Cys | Lys | Cys | Ser | |
| | | | | 100 | | | | | 105 | | | | | 110 | | |

TGA                                                                                                                                                                             339

( 2 ) INFORMATION FOR SEQ ID NO:30:

( i ) SEQUENCE CHARACTERISTICS:
         ( A ) LENGTH: 112 amino acids
         ( B ) TYPE: amino acid
         ( D ) TOPOLOGY: linear ( i i ) MOLECULE TYPE: protein ( x i ) SEQUENCE DESCRIPTION: SEQ ID NO:30:

Ala Leu Asp Thr Asn Tyr Cys Phe Ser Ser Thr Glu Lys Asn Cys Cys
 1               5                  10                  15

Val Arg Gln Leu Tyr Ile Asp Phe Arg Lys Asp Leu Gly Trp Lys Trp
             20                  25                  30

Ile His Glu Pro Lys Gly Tyr His Ala Asn Phe Cys Leu Gly Pro Cys
         35                  40                  45

| Pro | Tyr | Ile | Trp | Ser | Leu | Asp | Thr | Gln | Tyr | Ser | Lys | Val | Leu | Ala | Leu |
|---|---|---|---|---|---|---|---|---|---|---|---|---|---|---|---|
| | 50 | | | | | 55 | | | | 60 | | | | | |

| Tyr | Asn | Gln | His | Asn | Pro | Gly | Ala | Ser | Ala | Ala | Pro | Cys | Cys | Val | Pro |
|---|---|---|---|---|---|---|---|---|---|---|---|---|---|---|---|
| 65 | | | | | 70 | | | | 75 | | | | | | 80 |

| Gln | Ala | Leu | Glu | Pro | Leu | Pro | Ile | Val | Tyr | Tyr | Val | Gly | Arg | Lys | Pro |
|---|---|---|---|---|---|---|---|---|---|---|---|---|---|---|---|
| | | | | 85 | | | | | 90 | | | | | 95 | |

| Lys | Val | Glu | Gln | Leu | Ser | Asn | Met | Ile | Val | Arg | Ser | Cys | Lys | Cys | Ser |
|---|---|---|---|---|---|---|---|---|---|---|---|---|---|---|---|
| | | | 100 | | | | | 105 | | | | 110 | | | |

( 2 ) INFORMATION FOR SEQ ID NO:31:

( i ) SEQUENCE CHARACTERISTICS:
        ( A ) LENGTH: 339 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..336

( i x ) FEATURE:
        ( A ) NAME/KEY: mat_peptide
        ( B ) LOCATION: 1

( x i ) SEQUENCE DESCRIPTION: SEQ ID NO:31:

| GCT | TTG | GAT | GCG | GCC | TAT | TGC | TTT | AGA | AAT | GTG | CAG | GAT | AAT | TGC | TGC | 48 |
|---|---|---|---|---|---|---|---|---|---|---|---|---|---|---|---|---|
| Ala | Leu | Asp | Ala | Ala | Tyr | Cys | Phe | Arg | Asn | Val | Gln | Asp | Asn | Cys | Cys | |
| 1 | | | | 5 | | | | | 10 | | | | | 15 | | |

| CTA | CGT | CCA | CTT | TAC | ATT | GAT | TTC | AAG | AGG | GAT | CTA | GGG | TGG | AAA | TGG | 96 |
|---|---|---|---|---|---|---|---|---|---|---|---|---|---|---|---|---|
| Leu | Arg | Pro | Leu | Tyr | Ile | Asp | Phe | Lys | Arg | Asp | Leu | Gly | Trp | Lys | Trp | |
| | | | 20 | | | | | 25 | | | | | 30 | | | |

| ATA | CAC | GAA | CCC | AAA | GGG | TAC | AAT | GCC | AAC | TTC | TGT | GCT | GGA | GCA | TGC | 144 |
|---|---|---|---|---|---|---|---|---|---|---|---|---|---|---|---|---|
| Ile | His | Glu | Pro | Lys | Gly | Tyr | Asn | Ala | Asn | Phe | Cys | Ala | Gly | Ala | Cys | |
| | | 35 | | | | | 40 | | | | | 45 | | | | |

| CCG | TAT | TTA | TGG | AGT | TCA | GAC | ACT | CAG | CAC | AGC | AGG | GTC | CTG | AGC | TTA | 192 |
|---|---|---|---|---|---|---|---|---|---|---|---|---|---|---|---|---|
| Pro | Tyr | Leu | Trp | Ser | Ser | Asp | Thr | Gln | His | Ser | Arg | Val | Leu | Ser | Leu | |
| | 50 | | | | | 55 | | | | | 60 | | | | | |

| TAT | AAT | ACC | ATA | AAT | CCA | GAA | GCA | TCT | GCT | TCT | CCT | TGC | TGC | GTG | TCC | 240 |
|---|---|---|---|---|---|---|---|---|---|---|---|---|---|---|---|---|
| Tyr | Asn | Thr | Ile | Asn | Pro | Glu | Ala | Ser | Ala | Ser | Pro | Cys | Cys | Val | Ser | |
| 65 | | | | | 70 | | | | 75 | | | | | | 80 | |

| CAA | GAT | TTA | GAA | CCT | CTA | ACC | ATT | CTC | TAC | TAC | ATT | GGC | AAA | ACA | CCC | 288 |
|---|---|---|---|---|---|---|---|---|---|---|---|---|---|---|---|---|
| Gln | Asp | Leu | Glu | Pro | Leu | Thr | Ile | Leu | Tyr | Tyr | Ile | Gly | Lys | Thr | Pro | |
| | | | | 85 | | | | | 90 | | | | | 95 | | |

| AAG | ATT | GAA | CAG | CTT | TCT | AAT | ATG | ATT | GTA | AAG | TCT | TGC | AAA | TGC | AGC | 336 |
|---|---|---|---|---|---|---|---|---|---|---|---|---|---|---|---|---|
| Lys | Ile | Glu | Gln | Leu | Ser | Asn | Met | Ile | Val | Lys | Ser | Cys | Lys | Cys | Ser | |
| | | | 100 | | | | | 105 | | | | 110 | | | | |

| TAA | | | | | | | | | | | | | | | | 339 |
|---|---|---|---|---|---|---|---|---|---|---|---|---|---|---|---|---|

( 2 ) INFORMATION FOR SEQ ID NO:32:

( i ) SEQUENCE CHARACTERISTICS:
        ( A ) LENGTH: 112 amino acids
        ( B ) TYPE: amino acid
        ( D ) TOPOLOGY: linear ( i i ) MOLECULE TYPE: protein ( x i ) SEQUENCE DESCRIPTION: SEQ ID NO:32:

| Ala | Leu | Asp | Ala | Ala | Tyr | Cys | Phe | Arg | Asn | Val | Gln | Asp | Asn | Cys | Cys |
|---|---|---|---|---|---|---|---|---|---|---|---|---|---|---|---|
| 1 | | | | 5 | | | | | 10 | | | | | 15 | |

| Leu | Arg | Pro | Leu | Tyr | Ile | Asp | Phe | Lys | Arg | Asp | Leu | Gly | Trp | Lys | Trp |
|---|---|---|---|---|---|---|---|---|---|---|---|---|---|---|---|

```
                              20                         25                         30

Ile His Glu Pro Lys Gly Tyr Asn Ala Asn Phe Cys Ala Gly Ala Cys
                 35                      40                      45

Pro Tyr Leu Trp Ser Ser Asp Thr Gln His Ser Arg Val Leu Ser Leu
                 50                      55                      60

Tyr Asn Thr Ile Asn Pro Glu Ala Ser Ala Ser Pro Cys Cys Val Ser
         65                      70                      75                      80

Gln Asp Leu Glu Pro Leu Thr Ile Leu Tyr Tyr Ile Gly Lys Thr Pro
                         85                      90                      95

Lys Ile Glu Gln Leu Ser Asn Met Ile Val Lys Ser Cys Lys Cys Ser
                         100                     105                     110
```

( 2 ) INFORMATION FOR SEQ ID NO:33:

( i ) SEQUENCE CHARACTERISTICS:
       ( A ) LENGTH: 339 base pairs
       ( B ) TYPE: nucleic acid
       ( C ) STRANDEDNESS: double
       ( D ) TOPOLOGY: linear ( i i ) MOLECULE TYPE: cDNA ( i x ) FEATURE:
       ( A ) NAME/KEY: CDS
       ( B ) LOCATION: 1..336

( i x ) FEATURE:
       ( A ) NAME/KEY: mat_peptide
       ( B ) LOCATION: 1

( x i ) SEQUENCE DESCRIPTION: SEQ ID NO:33:

```
         GCT TTG GAC ACC AAT TAC TGC TTC CGC AAC TTG GAG GAG AAC TGC TGT        48
         Ala Leu Asp Thr Asn Tyr Cys Phe Arg Asn Leu Glu Glu Asn Cys Cys
         1               5                       10                      15

GTG CGC CCC CTC TAC ATT GAC TTC CGA CAG GAT CTG GGC TGG AAG TGG        96
         Val Arg Pro Leu Tyr Ile Asp Phe Arg Gln Asp Leu Gly Trp Lys Trp
                         20                      25                      30

GTC CAT GAA CCT AAG GGC TAC TAT GCC AAC TTC TGC TCA GGC CCT TGC       144
         Val His Glu Pro Lys Gly Tyr Tyr Ala Asn Phe Cys Ser Gly Pro Cys
                         35                      40                      45

CCA TAC CTC CGC AGT GCA GAC ACA ACC CAC AGC ACG GTG CTG GGA CTG       192
         Pro Tyr Leu Arg Ser Ala Asp Thr Thr His Ser Thr Val Leu Gly Leu
                 50                      55                      60

TAC AAC ACT CTG AAC CCT GAA GCA TCT GCC TCG CCT TGC TGC GTG CCC       240
         Tyr Asn Thr Leu Asn Pro Glu Ala Ser Ala Ser Pro Cys Cys Val Pro
         65                      70                      75                      80

CAG GAC CTG GAG CCC CTG ACC ATC CTG TAC TAT GTT GGG AGG ACC CCC       288
         Gln Asp Leu Glu Pro Leu Thr Ile Leu Tyr Tyr Val Gly Arg Thr Pro
                         85                      90                      95

AAA GTG GAG CAG CTC TCC AAC ATG GTG GTG AAG TCT TGT AAA TGT AGC       336
         Lys Val Glu Gln Leu Ser Asn Met Val Val Lys Ser Cys Lys Cys Ser
                         100                     105                     110

TGA                                                                  339
```

( 2 ) INFORMATION FOR SEQ ID NO:34:

( i ) SEQUENCE CHARACTERISTICS:
       ( A ) LENGTH: 112 amino acids
       ( B ) TYPE: amino acid
       ( D ) TOPOLOGY: linear ( i i ) MOLECULE TYPE: protein ( x i ) SEQUENCE DESCRIPTION: SEQ ID NO:34:

-continued

| | | | | | | | | | | | | | | |
|---|---|---|---|---|---|---|---|---|---|---|---|---|---|---|
| Ala 1 | Leu | Asp | Thr | Asn 5 | Tyr | Cys | Phe | Arg | Asn 10 | Leu | Glu | Glu | Asn | Cys Cys 15 |
| Val | Arg | Pro | Leu 20 | Tyr | Ile | Asp | Phe | Arg 25 | Gln | Asp | Leu | Gly | Trp 30 | Lys Trp |
| Val | His | Glu 35 | Pro | Lys | Gly | Tyr | Tyr 40 | Ala | Asn | Phe | Cys | Ser 45 | Gly | Pro Cys |
| Pro | Tyr 50 | Leu | Arg | Ser | Ala | Asp 55 | Thr | Thr | His | Ser | Thr 60 | Val | Leu | Gly Leu |
| Tyr 65 | Asn | Thr | Leu | Asn | Pro 70 | Glu | Ala | Ser | Ala | Ser 75 | Pro | Cys | Cys | Val Pro 80 |
| Gln | Asp | Leu | Glu | Pro 85 | Leu | Thr | Ile | Leu | Tyr 90 | Tyr | Val | Gly | Arg | Thr Pro 95 |
| Lys | Val | Glu | Gln 100 | Leu | Ser | Asn | Met | Val 105 | Val | Lys | Ser | Cys | Lys 110 | Cys Ser |